US011950163B2

(12) United States Patent
Loh et al.

(10) Patent No.: US 11,950,163 B2
(45) Date of Patent: Apr. 2, 2024

(54) CROWDSOURCED CONTACT TRACING

(71) Applicant: Expii Inc., Pittsburgh, PA (US)

(72) Inventors: Po-Shen Loh, Pittsburgh, PA (US);
Hannah Cai, San Jose, CA (US);
Felipe Campos, Midlothian, VA (US);
John Choi, Pittsburgh, PA (US);
Timothy Chu, San Jose, CA (US);
Dean Dijour, Morganville, NJ (US);
Bennett Huffman, Mequon, WI (US);
Mohammed Jaffer, San Bruno, CA (US); Ziv Scully, Pittsburgh, PA (US);
Brandon Wang, Saratoga, CA (US);
Lawrence Wang, New York, NY (US);
Phillip Wang, Irvine, CA (US)

(73) Assignee: Expii Inc., Pittsburgh, PA (US)

( * ) Notice: Subject to any disclaimer, the term of this patent is extended or adjusted under 35 U.S.C. 154(b) by 15 days.

(21) Appl. No.: 17/339,779

(22) Filed: Jun. 4, 2021

(65) Prior Publication Data
US 2021/0400428 A1 Dec. 23, 2021

Related U.S. Application Data

(60) Provisional application No. 63/111,486, filed on Nov. 9, 2020, provisional application No. 63/088,317, filed
(Continued)

(51) Int. Cl.
*G16H 50/80* (2018.01)
*G06T 11/20* (2006.01)
(Continued)

(52) U.S. Cl.
CPC ........... *H04W 4/023* (2013.01); *G06T 11/206* (2013.01); *G08B 5/22* (2013.01); *G16H 50/80* (2018.01)

(58) Field of Classification Search
CPC ..................................................... H04W 4/023
(Continued)

(56) References Cited

U.S. PATENT DOCUMENTS

| 7,729,204 B2 * | 6/2010 | Peng ....................... G01S 15/74 367/127 |
| 10,198,779 B2 * | 2/2019 | Pittman .................. G16H 50/80 |

(Continued)

OTHER PUBLICATIONS

Beeri, Tamar, *Israeli start-up to combat spread of coronavirus using touchless tech*, The Jerusalem Post, retrieved online from https://www.jpost.com/jpost-tech/israeli-start-up-to-combat-spread-of-coronavirus-using-touchless-tech-625703, Apr. 23, 2020 (3 pages).
(Continued)

*Primary Examiner* — Qutbuddin Ghulamali
(74) *Attorney, Agent, or Firm* — Fish & Richardson P.C.

(57) ABSTRACT

Systems and methods include the following. Information about a first electronic communication device is transmitted to at least one server and/or decentralized infrastructure. The information includes vicinity information. A status signal associated with a first user of the first electronic communication device is optionally transmitted. Contact proximity network information about a contact proximity network is received. The contact proximity network is based on the information from a plurality of electronic communication devices and information about the association between users and electronic communication devices. The contact proximity network information includes status signal information and interconnected nodes corresponding to different users and pairwise connections between users based upon their relative physical space and time proximity. A notification indicating a network-based proximity of a first user to a second user is provided, indicating a minimum number of connections between the first user and the second user during a specified time frame.

68 Claims, 9 Drawing Sheets

Related U.S. Application Data on Oct. 6, 2020, provisional application No. 63/087,800, filed on Oct. 5, 2020, provisional application No. 63/041,806, filed on Jun. 19, 2020.

(51) Int. Cl.
*G08B 5/22* (2006.01)
*H04W 4/02* (2018.01)

(58) Field of Classification Search
USPC .................................................. 455/456.1
See application file for complete search history.

(56) References Cited

U.S. PATENT DOCUMENTS

| | | | |
|---|---|---|---|
| 2003/0204130 | A1 | 10/2003 | Colston, Jr. et al. |
| 2010/0177699 | A1* | 7/2010 | Klefter ............... H04L 45/00 370/328 |
| 2013/0275160 | A1 | 10/2013 | Lev et al. |
| 2016/0274377 | A1* | 9/2016 | Toner ................. G02C 7/049 |
| 2018/0052970 | A1* | 2/2018 | Boss .................. G06F 21/35 |

OTHER PUBLICATIONS

Chandler, Simon, Forbes, *New Ultrasonic Contact-Tracing App Promises Better Accuracy Than Bluetooth Alternatives*, retrieved online from https://www.forbes.com/sites/simonchandler/2020/05/26/new-ultrasonic-contact-tracing-app-promises-better-accuracy-than-bluetooth-alternatives/?sh=21c90d832122. May 26, 2020 (5 pages).

Gates, *The first modern pandemic*, The Gates Notes, retrieved online from https://www.gatesnotes.com/Health/Pandemic-Innovation, Apr. 23, 2020 (16 pages).

Limor Joseph-Raz, *Sonarax ultrasonic solutions turns hands-on devices touchless amid coronavirus restrictions*, SONARAX.com, retrieved online from https://www.sonarax.com/post/sonarax-ultrasonic-solutions-turns-hands-on-devices-touchless-amid-coronavirus-restrictions. Apr. 23, 2020 (3 pages).

Novid, *FAQ*, NOVID.org, retrieved online from http://web.archive.org/web/20200407201051if_/https:/www.novid.org/faq, Apr. 7, 2020, (3 pages).

Novid, *Stop the Spread of COVID-19*, NOVID.org, retrieved online from http://web.archive.org/web/20200407200920/https:/www.novid.org/, Apr. 7, 2020 (6 pages).

Alsdurf et al., COVI White Paper—Version 1.1, Jul. 27, 2020, Retrieved on Mar. 1, 2023 from the Internet URL https://arxiv.org/abs/2005.08502 (64 pages).

Apple, Privacy-Preserving Contact Tracing, 2020; Retrieved on Mar. 1, 2023 from the Internet URL https://covid19.apple.com/contacttracing (1 page).

Chan et al., PACT: Privacy-Sensitive Protocols And Mechanisms for Mobile Contact Tracing, May 7, 2020, Retrieved from the Internet Mar. 1, 2023 URL https://arxiv.org/pdf/2004.03544.pdf (22 pages).

Loh, Po-Shen, Accuracy of Bluetooth-Ultrasound Contact Tracing: Experimental Results from NOVID iOS Version 2.1 Using Five-Year-Old Phones, Jun. 26, 2020; Retrieved on Mar. 1, 2023 from the Internet URL https ://protect-us.mimecast.com/s/U1BCCXD7q0h0JEo1skihxR?domain=novid.org (13 pages).

Loh, Po-Shen, Flipping the Perspective in Contact Tracing, Nov. 16, 2020, Retrieved from the Internet Mar. 1, 2023 URL https://arxiv.org/abs/2010.03806 (21 pages).

Meklenburg et al., SonicPACT: An Ultrasonic Ranging Method for the Private Automated Contact Tracing (PACT) Protocol, Dec. 8, 2020, Retrieved on Mar. 1, 2023 from the Internet URL https://arxiv.org/abs/2012.04770 (14 pages).

Mullin, Blyncsy's Patent On Contact Tracing Isn't A Medical Breakthrough, It's A Patent Breakdown, Jan. 20, 2021; Retrieved from the Internet on Mar. 1, 2023 URL https://www.eff.org/deeplinks/2021/01/blyncsys-patent-contact-tracing-isnt-medical-breakthrough-its-patent-breakdown.

Rivest et al., The PCT protocol specification, Apr. 8, 2020, Retrieved on Mar. 1, 2023 from the Internet URL https://pact.mit.edu/wp-content/nploads/2020/11/The-PACT-protocol-specification-2020.pdf (14 pages).

Troncoso et al., Decentralized Privacy-Preserving Proximity Tracing, May 25, 2020, Retrieved on Mar. 1, 2023 from the Internet URL https://github.com/DP-3T/documents/blob/master/DP3T%20White%20Paper.pdf (10 pages).

Unified Patents, $1,500 Awarded for Blyncsy prior art, Jan. 15, 2021, Retrieved from the Internet on May 2, 2023, URL https://www.unifiedpatents.com/insights/2021/1/15/1500-awarded-for-blyncsy-prior-art (5 pages).

Von Arx, Sydney, Slowing the Spread of Infectious Diseases Using Crowd sou reed Data, Covid Watch, Mar. 20, 2020; Retrieved on Mar. 1, 2023 from the Internet URL https://f.hubspotusercontent30.net/hubfs/7663287/Collateral/covid_watch_whitepaper.pdf (10 pages).

YouTube video clip: Pittsburgh Technology Counsel, Comcast Summer of PHG Tech Stories, Summer of Stories Ep. 1: Po-Shen Loh of Expii Interview; uploaded on Jun. 10, 2020 by user Po-Shen Loh, Retrieved from the Internet May 2, 2023, URL https://www.youtube.com/watch?v=3wjTsoOZ1Ik (1 page).

YouTube video clip: Daily Challenge with Po-Shen Loh, North South Foundation Seminar: From Math Contests to Fighting COVID-19; uploaded on Jun. 7, 2020 by user Po-Shen Loh, Retrieved from the Internet May 2, 2023, URL https://www.youtube.com/watch?v=my1WTJ7tx6E (1 page).

Anonymous: "Corona-Warn-App Solution Architecture", Jun. 3, 2020, XP055843646, Retrieved from the Internet: URL:https://github.com/corona-warn-app/cwa-documentation/blob/2c61f7f4758c0fee9b3768d9880fa6f8d98a7131/solution_architecture.md [retrieved on Sep. 22, 2021].

Anonymous: "Corona-Warn-App User Interface Screens", May 29, 2020, XP055843651, Retrieved from the Internet: URL:https://github.com/corona-warn-app/cwa-documentation/blob/2c61f7f4758c0fee9b3768d9880fa6f8d98a7131/ui_screens.md [retrieved on Sep. 22, 2021].

Anonymous: "cwa-documentation/scoping_document.md at 2c61f7f4758c0fee9b3768d9880fa6f8d98a7131.corona-warn-app/cwa-documentation. GitHub", May 26, 2020, XP055843653, Retrieved from the Internet: URL:https://github.com/corona-warn-app/cwa-documentation/blob/2c61f7f4758c0fee9b3768d9880fa6f8d98a7131/scoping_document.md [retrieved on Sep. 22, 2021].

Anonymous: "Open-Source Project Corona-Warn-App", Jun. 2, 2020, XP055843638, Retrieved from the Internet: URL:https://web.archive.org/web/20200602090626/https://www.coronawarn.app/en/ [retrieved on Sep. 22, 2021].

Mueller Juergen: "Die Technik hinter der Corona-Warn-App | SAP News Center", May 20, 2020, XP055843662, Retrieved from the Internet: URL:https://news.sap.com/germany/2020/05/covid19-technischegrundlage-corona-warn-app/ [retrieved on Sep. 22, 2021].

PCT International Search Report and Written Opinion in International Appln. PCT/US2021/037827, dated Oct. 6, 2021, 17 pages.

* cited by examiner

```
┌─────────────────────────────────────────────────────────────────────┐
│ Transmit, to at least one server and/or decentralized infrastructure and from a first │
│ electronic communication device, information about the first electronic communication │
│ device, where the information about the first electronic communication │
│ device comprises vicinity information about a vicinity of the first electronic communication │
│                              device                                302 │
└─────────────────────────────────────────────────────────────────────┘
                                    │
                                    ▼
┌─────────────────────────────────────────────────────────────────────┐
│ Optionally transmit, to the at least one server and/or decentralized infrastructure and │
│ from the first electronic communication device, a status signal associated with a first │
│          user of the first electronic communication device         304 │
└─────────────────────────────────────────────────────────────────────┘
                                    │
                                    ▼
┌─────────────────────────────────────────────────────────────────────┐
│ Receive and store contact proximity network information about a contact proximity │
│ network from the at least one server and/or decentralized infrastructure, where the │
│ contact proximity network is based, in part, on the information from a plurality of │
│ electronic communication devices and information about the association between users │
│ and electronic communication devices, where the contact proximity network information │
│ comprises status signal information associated with users within the contact proximity │
│ network, and where the contact proximity network comprises a plurality of │
│ interconnected nodes, where each node of the plurality of interconnected nodes │
│ corresponds to a different user and each pairwise connection between two users in the │
│ contact proximity network is based in part upon their current or past relative physical │
│                      space and time proximity                      306 │
└─────────────────────────────────────────────────────────────────────┘
                                    │
                                    ▼
┌─────────────────────────────────────────────────────────────────────┐
│ Provide, using the contact proximity network information received from the at least one │
│ server and/or decentralized infrastructure, a user notification indicating a network-based │
│ proximity of a first user in the contact proximity network to a second user in the contact │
│ proximity network, where the second user is identified as associated with a specified │
│ status signal within a specified time frame, where the network-based proximity of the │
│ first user to the second user is a minimum number of connections between the first user │
│ and the second user along the contact proximity network during the specified time │
│                              frame                                 308 │
└─────────────────────────────────────────────────────────────────────┘
```

FIG. 3

CROWDSOURCED CONTACT TRACING

CROSS-REFERENCE TO RELATED APPLICATIONS

This application is a conversion of Provisional Application No. 63/041,806, filed on Jun. 19, 2020; Provisional Application No. 63/087,800, filed on Oct. 5, 2020; Provisional Application No. 63/088,317 filed on Oct. 6, 2020; and Provisional Application No. 63/111,486, filed on Nov. 9, 2020; each application hereby incorporated by reference in its entirety.

TECHNICAL FIELD

The present disclosure applies to determining and providing information about user interactions with other users.

BACKGROUND

The mass proliferation of greater and greater generations of smartphones provides an array of useful sensors and a variety of short-range communication capabilities. The information can be used to determine information from close-physical-proximity interactions on individual mobile devices. Information from multiple users can be aggregated using an aggregation framework.

SUMMARY

The present disclosure describes techniques that can be used for determining user interactions with others, and communicating information (in graphical, text, or other forms) which takes that interaction network into account. For example, the techniques can be used to create a chart showing a user their relative network-theoretic distance (e.g., a shortest path or a least number of edges on a connecting path, also abbreviated as "network-distance" in this document) from other users who are identified as exposure risks to a virus.

The previously described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method, the instructions stored on the non-transitory, computer-readable medium.

Described implementations of the subject matter can include one or more features, alone or in combination.

For example, in a first implementation, a computer-implemented method includes the following. Information about a first electronic communication device is transmitted from the first electronic communication device to at least one server and/or decentralized infrastructure. The information about the first electronic communication device includes vicinity information about a vicinity of the first electronic communication device. A status signal associated with a first user of the first electronic communication device is optionally transmitted from the first electronic communication device to the at least one server and/or decentralized infrastructure. Contact proximity network information about a contact proximity network is received from the at least one server and/or decentralized infrastructure and is stored. The contact proximity network is based, in part, on the information from a plurality of electronic communication devices and information about the association between users and electronic communication devices. The contact proximity network information includes status signal information associated with users within the contact proximity network. The contact proximity network includes a plurality of interconnected nodes, where each node of the plurality of interconnected nodes corresponds to a different user and each pairwise connection between two users in the contact proximity network is based in part upon their current or past relative physical space and time proximity. A user notification indicating a network-based proximity of a first user in the contact proximity network to a second user in the contact proximity network is provided using the contact proximity network information received from the at least one server and/or decentralized infrastructure. The second user is identified as associated with a specified status signal within a specified time frame. The network-based proximity of the first user to the second user is a minimum number of connections between the first user and the second user along the contact proximity network during the specified time frame.

The foregoing and other described implementations can each, optionally, include one or more of the following features:

A first feature, combinable with any of the following features, where the vicinity information for the first electronic communication device includes information about a second electronic communication device, where the information about the second electronic communication device includes data regarding a proximity or location of the first electronic communication device relative to the second electronic communication device, and where the method further includes transmitting the information about the second electronic communication device to the at least one server and/or decentralized infrastructure.

A second feature, combinable with any of the previous or following features, where the specified status signal is positivity for a contagion.

A third feature, combinable with any of the previous or following features, where the status signal is being a physical contact of a person who is positive for a contagion, or more generally, being less than or equal to a specified number of physical contacts separated from a person who is positive for a contagion.

A fourth feature, combinable with any of the previous or following features, where the user notification is one or more of a text, an animation, and a graphical display.

A fifth feature, combinable with any of the previous or following features, where the graphical display includes information about a dynamically updatable contact proximity network, and where that information includes bars graphically summarizing connections among nodes in the contact proximity network.

A sixth feature, combinable with any of the previous or following features, where obtaining information about the second electronic communication device includes estimating a physical distance between the first electronic communication device and the second electronic communication device based on one or more of an audio signal, a radio-frequency signal, an infrared signal, and an optical signal emitted by one or more of the first electronic communication device and by the second electronic communication device; and/or by signals between the first and second electronic communication devices and other electronic communication device(s) which are used to estimate the distance between the first and second electronic communication devices.

A seventh feature, combinable with any of the previous or following features, where the contact proximity network illustrates a time-evolution of contact network distance(s) from the first user to other users reporting status signals during time windows of interest.

An eighth feature, combinable with any of the previous or following features, where the vicinity information includes information about a second electronic communication device that includes one or more of: a physical distance of the second electronic communication device from the first electronic communication device; and data about audio, radio-frequency, optical, and/or infrared signals emitted by one or both of the second electronic communication device and the first electronic communication device.

A ninth feature, combinable with any of the previous or following features, where the contact proximity network traces a spread through the contact proximity network, of users reporting a specified status signal.

A tenth feature, combinable with any of the previous or following features, where the contact proximity network represents pairwise interactions between users, where the contact proximity network includes proximity information amongst a plurality of users associated with a plurality of electronic communication devices, where the proximity information includes a geographical distance, a network distance along the contact proximity network, and/or frequency of contact between users' associated electronic communication devices, and where the proximity information includes one or more of: current geographical distance between users' associated electronic communication devices, and/or a current network distance between users; past geographical distance between users' associated electronic communication devices, and/or a network distance between users during a past period of time; time information related to when users' associated electronic communication devices were within a defined vicinity relative to one another; and/or duration information related to how long users' associated electronic communication devices were within the defined vicinity relative to one another.

An eleventh feature, combinable with any of the previous or following features, further including deriving a predicted spread of users reporting a specified status signal along at least part of the contact proximity network.

A twelfth feature, combinable with any of the previous or following features, further including outputting a time-evolution graphic depicting a spread of users reporting a specified status signal along at least part of the contact proximity network, where the time-evolution graphic includes a representation of a number of users reporting a specified status signal within a specified time window as a function of network distance along the contact proximity network.

A thirteenth feature, combinable with any of the previous or following features, further including identifying and/or outputting a post-exposure notification to users exposed to a user reporting a specified status signal within a specified time frame.

A fourteenth feature, combinable with any of the previous or following features, further including determining a duration over which the first electronic communication device is within a predefined vicinity of a second electronic communication device.

A fifteenth feature, combinable with any of the previous or following features, further including transmitting, to at least one server, information about at least one user, where the information includes an indicator to report specified status signal(s) on behalf of and associated with the at least one user.

A sixteenth feature, combinable with any of the previous or following features, further including transmitting, by a third electronic communication device, an indicator that at least one user of the contact proximity network reports specified status signal(s).

A seventeenth feature, combinable with any of the previous or following features, further including assigning a trusted authentication rating to the indicator received from the third electronic communication device.

An eighteenth feature, combinable with any of the previous or following features, further including outputting an exposure notification indicative of a first user's contact proximity to a second user reporting a specified status signal, where the contact proximity to the second user includes a geographical distance and/or a network distance along the contact proximity network between the two users.

In a second implementation, a computer-implemented system includes one or more electronic processors and one or more computer memory devices interoperably coupled with the one or more electronic processors and having tangible, non-transitory, machine-readable media storing one or more instructions that, when executed by the one or more electronic processors, perform one or more operations including the following. Information about a first electronic communication device is transmitted from the first electronic communication device to at least one server and/or decentralized infrastructure. The information about the first electronic communication device includes vicinity information about a vicinity of the first electronic communication device. A status signal associated with a first user of the first electronic communication device is optionally transmitted from the first electronic communication device to the at least one server and/or decentralized infrastructure. Contact proximity network information about a contact proximity network is received from the at least one server and/or decentralized infrastructure and is stored. The contact proximity network is based, in part, on the information from a plurality of electronic communication devices and information about the association between users and electronic communication devices. The contact proximity network information includes status signal information associated with users within the contact proximity network. The contact proximity network includes a plurality of interconnected nodes. Each node of the plurality of interconnected nodes corresponds to a different user. Each pairwise connection between two users in the contact proximity network is based in part upon their current or past relative physical space and time proximity. A user notification indicating a network-based proximity of a first user in the contact proximity network to a second user in the contact proximity network is provided using the contact proximity network information received from the at least one server and/or decentralized infrastructure. The second user is identified as associated with a specified status signal within a specified time frame. The network-based proximity of the first user to the second user is a minimum number of connections between the first user and the second user along the contact proximity network during the specified time frame.

The foregoing and other described implementations can each, optionally, include one or more of the following features:

A first feature, combinable with any of the following features, where the vicinity information for the first electronic communication device includes information about a second electronic communication device, where the information about the second electronic communication device includes data regarding a proximity or location of the first electronic communication device relative to the second electronic communication device, and where the operations further includes transmitting the information about the second electronic communication device to the at least one server and/or decentralized infrastructure.

A second feature, combinable with any of the previous or following features, where the specified status signal is positivity for a contagion.

A third feature, combinable with any of the previous or following features, where the status signal is being a physical contact of a person who is positive for a contagion, or more generally, being less than or equal to a specified number of physical contacts separated from a person who is positive for a contagion.

A fourth feature, combinable with any of the previous or following features, where the user notification is one or more of a text, an animation, and a graphical display.

A fifth feature, combinable with any of the previous or following features, where the graphical display includes information about a dynamically updatable contact proximity network, and where that information includes bars graphically summarizing connections among nodes in the contact proximity network.

A sixth feature, combinable with any of the previous or following features, where obtaining information about the second electronic communication device includes estimating a physical distance between the first electronic communication device and the second electronic communication device based on one or more of an audio signal, a radio-frequency signal, an infrared signal, and an optical signal emitted by one or more of the first electronic communication device and by the second electronic communication device, and/or by signals between the first and second electronic communication devices and other electronic communication device(s) which are used to estimate the distance between the first and second electronic communication devices.

A seventh feature, combinable with any of the previous or following features, where the contact proximity network illustrates a time-evolution of contact network distance(s) from the first user to other users reporting status signals during time windows of interest.

An eighth feature, combinable with any of the previous or following features, where the vicinity information includes information about a second electronic communication device that includes one or more of: a physical distance of the second electronic communication device from the first electronic communication device; and data about audio, radio-frequency, optical, and/or infrared signals emitted by one or both of the second electronic communication device and the first electronic communication device.

A ninth feature, combinable with any of the previous or following features, where the contact proximity network traces a spread through the contact proximity network, of users reporting a specified status signal.

A tenth feature, combinable with any of the previous or following features, where the contact proximity network represents pairwise interactions between users, where the contact proximity network includes proximity information amongst a plurality of users associated with a plurality of electronic communication devices, where the proximity information includes a geographical distance, a network distance along the contact proximity network, and/or frequency of contact between users' associated electronic communication devices, and where the proximity information includes one or more of: current geographical distance between users' associated electronic communication devices, and/or a current network distance between users; past geographical distance between users' associated electronic communication devices, and/or a network distance between users during a past period of time; time information related to when users' associated electronic communication devices were within a defined vicinity relative to one another; and/or duration information related to how long users' associated electronic communication devices were within the defined vicinity relative to one another.

An eleventh feature, combinable with any of the previous or following features, the operations further including deriving a predicted spread of users reporting a specified status signal along at least part of the contact proximity network.

A twelfth feature, combinable with any of the previous or following features, the operations further including outputting a time-evolution graphic depicting a spread of users reporting a specified status signal along at least part of the contact proximity network, where the time-evolution graphic includes a representation of a number of users reporting a specified status signal within a specified time window as a function of network distance along the contact proximity network.

A thirteenth feature, combinable with any of the previous or following features, the operations further including identifying and/or outputting a post-exposure notification to users exposed to a user reporting a specified status signal within a specified time frame.

A fourteenth feature, combinable with any of the previous or following features, the operations further including determining a duration over which the first electronic communication device is within a predefined vicinity of a second electronic communication device.

A fifteenth feature, combinable with any of the previous or following features, the operations further including transmitting, to at least one server, information about at least one user, where the information includes an indicator to report specified status signal(s) on behalf of and associated with the at least one user.

A sixteenth feature, combinable with any of the previous or following features, the operations further including transmitting, by a third electronic communication device, an indicator that at least one user of the contact proximity network reports specified status signal(s).

A seventeenth feature, combinable with any of the previous or following features, the operations further including assigning a trusted authentication rating to the indicator received from the third electronic communication device.

An eighteenth feature, combinable with any of the previous or following features, the operations further including outputting an exposure notification indicative of a first user's contact proximity to a second user reporting a specified status signal, where the contact proximity to the second user includes a geographical distance and/or a network distance along the contact proximity network between the two users.

In a third implementation, a computer-implemented method includes the following. Information about a first electronic communication device is obtained from a first electronic communication device by at least one server and/or decentralized infrastructure. The information about the first electronic communication device includes vicinity information about a vicinity of the first electronic communication device. A status signal associated with a first user of the first electronic communication device is optionally obtained. A contact proximity network is generated and/or updated by the at least one server and/or decentralized infrastructure based, in part, on the information from the first electronic communication device, optionally including information about a second electronic communication device, and optionally including the status signal associated with the first user. The contact proximity network is stored. The contact proximity network includes a plurality of interconnected nodes, where each node of the plurality of interconnected nodes corresponds to a different user and each pairwise connection between two users in the contact proximity network is based in part upon their current or past relative physical space and time proximity. Contact proximity network information about the contact proximity network is provided to the first electronic communication device by the at least one server and/or decentralized infrastructure. The contact proximity network information includes status signal information associated with users within the contact proximity network. The contact proximity information includes a user notification indicating a network-based proximity of a first user in the contact proximity network to a second user in the contact proximity network. The second user is identified as associated with a specified status signal within a specified time frame. The network-based proximity of the first user to the second user is a minimum number of connections between the first user and the second user along the contact proximity network during the specified time frame.

The foregoing and other described implementations can each, optionally, include one or more of the following features:

A first feature, combinable with any of the following features, where the vicinity information about the vicinity of the first electronic communication device includes location information of the first electronic communication device.

A second feature, combinable with any of the previous or following features, where the vicinity information about the vicinity of the first electronic communication device includes data about an environment in which the first electronic communication device is located.

A third feature, combinable with any of the previous or following features, where the vicinity information about the vicinity of the first electronic communication device includes information about a second electronic communication device.

A fourth feature, combinable with any of the previous or following features, where the information about the second electronic communication device includes a physical distance of the first electronic communication device to the second electronic communication device.

A fifth feature, combinable with any of the previous or following features, where the information about the second electronic communication device includes information about a wireless local area network, about a wireless access point, or about an electronic communication device in the vicinity of the first electronic communication device.

A sixth feature, combinable with any of the previous or following features, where obtaining the status signal associated with a first user of the first electronic communication device includes receiving the status signal from the first electronic communication device or receiving the status signal from a third electronic communication device.

A seventh feature, combinable with any of the previous or following features, where obtaining the status signal associated with a first user of the first electronic communication device includes receiving a trusted authentication token, where the trusted authentication token authenticates the status signal associated with the first user.

An eighth feature, combinable with any of the previous or following features, where generating and storing the contact proximity network includes determining a duration over which the first electronic communication device is within a predefined vicinity of the second electronic communication device.

A ninth feature, combinable with any of the previous or following features, where the user notification is one or more of a text, an animation, and a graphical display.

A tenth feature, combinable with any of the previous or following features, where the user notification is a graphical display that includes a dynamically updatable chart including bars graphically summarizing the network-based proximity of the first user in the contact proximity network to at least one other user identified as associated with the specified status signal within the specified time frame.

An eleventh feature, combinable with any of the previous or following features, further including the contact proximity network represents pairwise proximal interactions between users, where the contact proximity network includes proximity information amongst a plurality of users associated with a plurality of electronic communication devices, where the proximity information includes a geographical distance, a network distance along the contact proximity network, and/or frequency of contact between users' associated electronic communication devices, and where the proximity information includes one or more of: current geographical distance between users' associated electronic communication devices, and/or a current network distance between users; past geographical distance between users' associated electronic communication devices, and/or a network distance between users during a past period of time; time information related to when users' associated electronic communication devices were within a defined vicinity relative to one another; and/or duration information related to how long users' associated electronic communication devices were within the defined vicinity relative to one another.

A twelfth feature, combinable with any of the previous or following features, where the user notification includes a predicted spread of users reporting a specified status signal along at least part of the contact proximity network.

A thirteenth feature, combinable with any of the previous or following features, further including outputting a time-evolution graphic depicting a spread of users reporting a specified status signal along at least part of the contact proximity network, where the time-evolution graphic includes a representation of a number of users reporting a specified status signal within the specified time frame as a function of network distance along the contact proximity network.

A fourteenth feature, combinable with any of the previous or following features, further including identifying and/or outputting a post-exposure notification to users exposed to a user reporting a specified status signal within a specified time frame.

In a fourth implementation, a computer-implemented system includes one or more electronic processors and one or more computer memory devices interoperably coupled with the one or more electronic processors and having tangible, non-transitory, machine-readable media storing one or more instructions that, when executed by the one or more electronic processors, perform one or more operations including the following. Information about a first electronic communication device is obtained from a first electronic communication device by at least one server and/or decentralized infrastructure. The information about the first electronic communication device includes vicinity information about a vicinity of the first electronic communication device. A status signal associated with a first user of the first electronic communication device is optionally obtained. A contact proximity network is generated and/or updated by the at least one server and/or decentralized infrastructure based, in part, on the information from the first electronic communication device, optionally including information about a second electronic communication device, and optionally including the status signal associated with the first use. The contact proximity network is stored. The contact proximity network includes a plurality of interconnected nodes, where each node of the plurality of interconnected nodes corresponds to a different user and each pairwise connection between two users in the contact proximity network is based in part upon their current or past relative physical space and time proximity. Contact proximity network information about the contact proximity network is provided to the first electronic communication device by the at least one server and/or decentralized infrastructure. The contact proximity network information includes status signal information associated with users within the contact proximity network. The contact proximity information includes a user notification indicating a network-based proximity of a first user in the contact proximity network to a second user in the contact proximity network. The second user is identified as associated with a specified status signal within a specified time frame. The network-based proximity of the first user to the second user is a minimum number of connections between the first user and the second user along the contact proximity network during the specified time frame.

The foregoing and other described implementations can each, optionally, include one or more of the following features:

A first feature, combinable with any of the following features, where the vicinity information about the vicinity of the first electronic communication device includes location information of the first electronic communication device.

A second feature, combinable with any of the previous or following features, where the vicinity information about the vicinity of the first electronic communication device includes data about an environment in which the first electronic communication device is located.

A third feature, combinable with any of the previous or following features, where the vicinity information about the vicinity of the first electronic communication device includes information about a second electronic communication device.

A fourth feature, combinable with any of the previous or following features, where the information about the second electronic communication device includes a physical distance of the first electronic communication device to the second electronic communication device.

A fifth feature, combinable with any of the previous or following features, where the information about the second electronic communication device includes information about a wireless local area network, about a wireless access point, or about an electronic communication device in the vicinity of the first electronic communication device.

A sixth feature, combinable with any of the previous or following features, where obtaining the status signal associated with a first user of the first electronic communication device includes receiving the status signal from the first electronic communication device or receiving the status signal from a third electronic communication device.

A seventh feature, combinable with any of the previous or following features, where obtaining the status signal associated with a first user of the first electronic communication device includes receiving a trusted authentication token, where the trusted authentication token authenticates the status signal associated with the first user.

An eighth feature, combinable with any of the previous or following features, where generating and storing the contact proximity network includes determining a duration over which the first electronic communication device is within a predefined vicinity of the second electronic communication device.

A ninth feature, combinable with any of the previous or following features, where the user notification is one or more of a text, an animation, and a graphical display.

A tenth feature, combinable with any of the previous or following features, where the user notification is a graphical display that includes a dynamically updatable chart including bars graphically summarizing the network-based proximity of the first user in the contact proximity network to at least one other user identified as associated with the specified status signal within the specified time frame.

An eleventh feature, combinable with any of the previous or following features, the operations further including the contact proximity network represents pairwise proximal interactions between users, where the contact proximity network includes proximity information amongst a plurality of users associated with a plurality of electronic communication devices, where the proximity information includes a geographical distance, a network distance along the contact proximity network, and/or frequency of contact between users' associated electronic communication devices, and where the proximity information includes one or more of: current geographical distance between users' associated electronic communication devices, and/or a current network distance between users; past geographical distance between users' associated electronic communication devices, and/or a network distance between users during a past period of time; time information related to when users' associated electronic communication devices were within a defined vicinity relative to one another; and/or duration information related to how long users' associated electronic communication devices were within the defined vicinity relative to one another.

A twelfth feature, combinable with any of the previous or following features, where the user notification includes a predicted spread of users reporting a specified status signal along at least part of the contact proximity network.

A thirteenth feature, combinable with any of the previous or following features, the operations further including outputting a time-evolution graphic depicting a spread of users reporting a specified status signal along at least part of the contact proximity network, where the time-evolution graphic includes a representation of a number of users reporting a specified status signal within the specified time frame as a function of network distance along the contact proximity network.

A fourteenth feature, combinable with any of the previous or following features, the operations further including identifying and/or outputting a post-exposure notification to users exposed to a user reporting a specified status signal within a specified time frame.

The subject matter described in this specification can be implemented in particular implementations, so as to realize one or more of the following advantages. Users can be notified, through the display of a radar visual, regarding their status of being a certain number of connections away from each of potential health threats presented by others.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

FIG. 3 is a flowchart of an example of a method for providing a pre-exposure warning system, according to some implementations of the present disclosure.

Like reference numbers and designations in the various drawings indicate like elements.

DETAILED DESCRIPTION

Figure 1A:
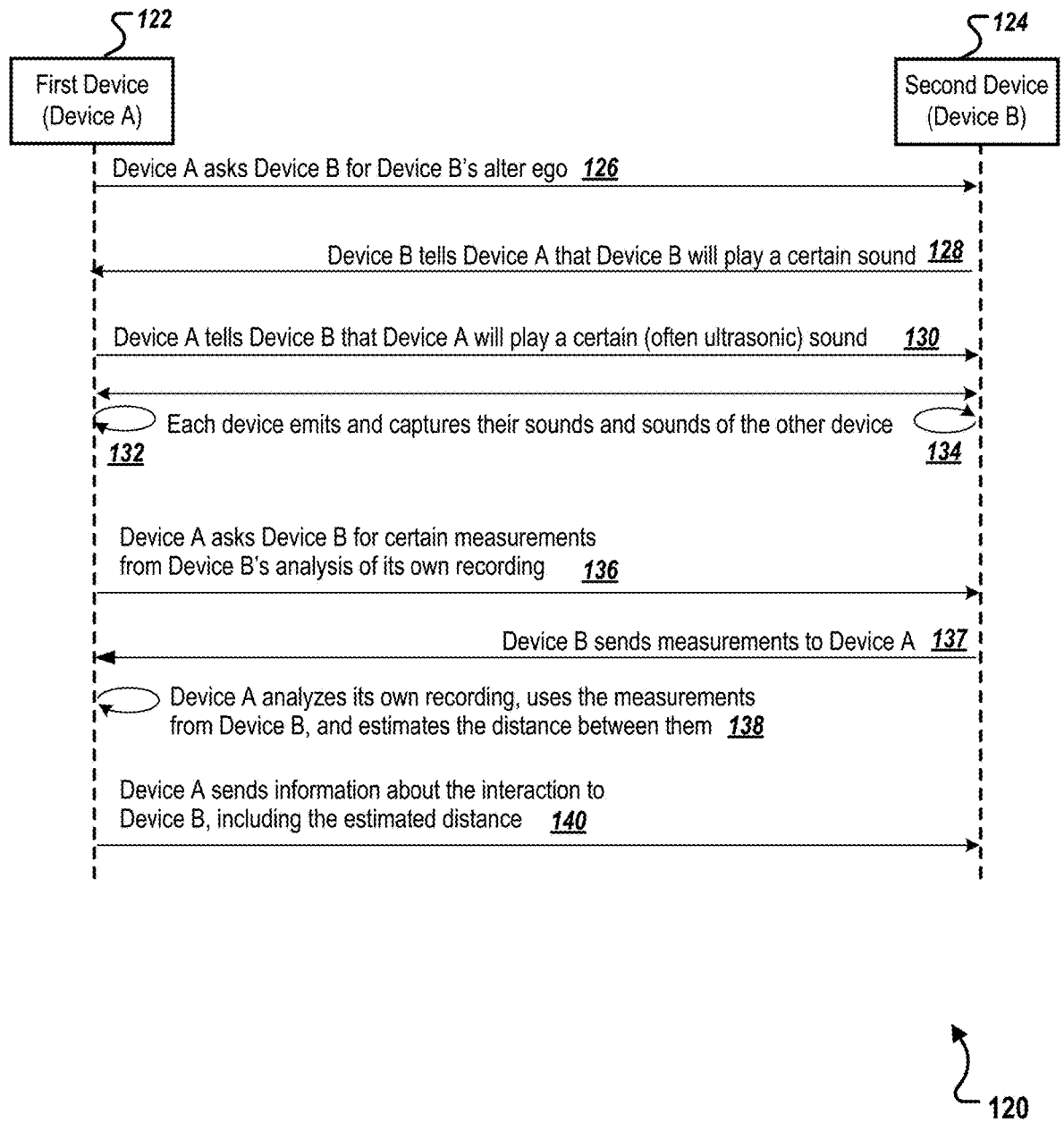
FIG. 1A is a swim lane diagram showing an example of a dialogue between devices used in the present disclosure, according to some implementations of the present disclosure.

The following detailed description describes techniques for providing a pre-exposure warning system. Various modifications, alterations, and permutations of the disclosed implementations can be made and will be readily apparent to those of ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

In some implementations, the pre-exposure warning system can be implemented as way to: collect information for and generate a proximity network composed of nodes and vertices, label various nodes with status signals, and communicate the status signals to the users in terms of a network-theoretic distance in the proximity network. The phrase "in terms of" indicates, for example, that the communication can use the network-theoretic distance as one of the factors or components in the communication, but other factors can be used as well. For example, information that is communicated can take into account both the date of the status signal and the network-theoretic distance between the user and the status signal.

INTRODUCTION

This disclosure describes a system which unlocks an alternative parallel pathway for contact tracing applications in the context of infectious disease. Conventional systems may be used for identifying positive cases after confirmation of infection, and tracing and quarantining possibly infected contacts. However, this system uses an accurate sensing protocol among a distributed deployment of mobile devices to crowdsource a close-physical-proximity interaction network. As such, this system can propagate early warning of approaching infections so that uninfected individuals can take precautions to protect themselves from ever being infected. More broadly, this system naturally adapts to more general settings which involve the propagation of status signals for which the close-physical-proximity interaction network has particular relevance. Several elements of this approach are novel, including the use of common on-board smartphone capabilities to engage short-range communication such as BLUETOOTH (providing a coarse distance estimate using communication signal strength and transmission power), optionally followed by more accurate ultrasound-based distance estimation. This type of distance is a physical distance between two devices. The acoustic distance estimation system also includes a novel communication signal design (e.g., acoustic) and digital signal processing for more noise-tolerant operation near the Nyquist (upper) frequency limit among mostly-at-rest devices. The system also includes the interpretation of the collected status signals in terms of network-theoretic distances on the interaction network.

This disclosure describes a system for interrupting the spread of a contagious disease, using crowdsourced information from an array of users with mobile devices to directly help each user avoid infection. The system leverages individual motivations for self-protection, providing advance warning so that the community as a whole dynamically modulates behavior in a way that substantially reduces the spread of the infection. The system is designed so that it supports implementations in which all users participate anonymously, with no personal identifying information (PII) collected. This system also supports non-anonymous implementations. More generally, this system can be applied in any other context which involves status signals propagating along the network of close-proximity physical interactions.

The system has several types of agents, including the following. In some implementations, a central authority makes policy decisions on the parameters and mode of operation of the entire system, including models of data transfer, storage, and computation. Ordinary users include trusted users who are trusted by the central authority to confirm the authenticity of reported information. These agents participate in a system including several major components, including the following three subsystems.

An Interaction Collection Subsystem can be used to collect records of interactions between pairs (or in some implementations, triplets, and quadruplets, etc.) of devices. The records include information labels which may include the time of interaction, the estimated physical distance between the devices, and metadata to aid in estimating interaction duration. To support devices which may not be able to communicate with other devices (e.g., due to a mobile operating system not permitting full operation in the background), devices can also report their sensing of the environment, not limited to nearby WiFi access point service set identifiers (SSIDs), basic service set identifiers (BSSIDs), nearby BLUETOOTH MAC addresses, or GPS coordinates (optionally hashed for privacy). As other communication methods and sensors become available, this approach can be extended to natural generalizations. For example, ULTRA-WIDEBAND may be used for radio-frequency communication instead of (or alongside) BLUETOOTH; even though much of this disclosure is written in terms of BLUETOOTH, natural generalizations to ULTRA-WIDEBAND or other communication methods are permissible.

A Status Signal Collection Subsystem can be used to collect status signals. The status signals can be in many forms. Some examples of status signals in the context of contact tracing include self-reported positive tests and/or confirmations of positive tests using one-time tokens from trusted users. Status signal information that is collected can also include confirmations of contact with confirmed positive cases (optionally using one-time tokens from trusted users), symptom surveys, vaccinations, data from sensors (onboard or external), or direct input by trusted users. Natural generalizations to other application domains are possible.

A Notification Calculation and Delivery Subsystem can use the collected status signals to create and send notification messages, for example, which can be displayed as animations, text, or images, or in other forms, on the user's device, or via other methods such as text messages, phone calls, email messages, separate web portals, etc. In an example in the context of contact tracing, some of the notification messages can be pre-exposure warnings to alert a not-yet-exposed user to take precautions to avoid getting exposed. Some of the notification messages can be post-exposure warnings to request that a potentially exposed user self-isolate to prevent others from getting exposed. Natural generalizations to other application domains are possible.

Interaction Collection Subsystem

Modern smartphones and electronic devices (e.g., accessories) contain an array of useful sensors and possess a variety of short-range communication capabilities. The system described in greatest detail in this disclosure has a central authority which oversees the collection of information records from participating devices, which can be used to reconstruct the network of close-physical-proximity interactions. However, the algorithms which calculate the network-theoretic distances from users to status signals naturally generalize to decentralized computation (the update steps in the algorithm consist of bitwise OR's of data with neighboring nodes), so decentralized implementations of this general new concept of projecting status signals onto network-theoretic distance are possible. Therefore, this disclosure also provides detail to support decentralized implementations as well, by supplying specific instructions for decentralization throughout this disclosure. This subsystem breaks into two parts: the individual mobile devices and the aggregation framework (which may be centralized or decentralized). Collecting and processing the information can provide a powerful opportunity, for example, to control the spread of infectious disease, providing an alternative parallel pathway for contact tracing.

Mobile Devices

Each participating device that participates in the system can have a unique identifier (ID). Devices may be smartphones or other electronic devices with communication or logging capabilities (e.g., similar to APPLE's AIRTAG or a BLUETOOTH or ULTRA-WIDEBAND or GPS capable dongle). The devices may communicate with nearby smartphones or servers to facilitate their participation, including possibly relying on computation by devices owned or operated by others. For example, a device can send and/or listen for signals via BLUETOOTH or ULTRA-WIDEBAND with nearby devices, and optionally rely on nearby electronic devices and/or remote servers to contribute computations that combine the received signal strength indicators from all of these signals (possibly with additional information) to triangulate devices' locations relative to other devices, or even their absolute locations. The aforementioned triangulation process does not even require that all pairwise distances are directly estimated among a collection of nearby devices. As an example, if Devices A, B, C, and D have estimates of their six pairwise distances between each other, then that already determines the relative position of those four devices (six side lengths determine a tetrahedron); then, even if there is no distance estimate between Devices E and F, but there are distance estimates between Device E and all of Devices A, B, C, and D, and also distance estimates between Device F and all of Devices A, B, C, and D, then the positions of Devices E and F relative to the tetrahedron among Devices A, B, C, and D are known, allowing the deduction of an estimate of the distance between Devices E and F. In some implementations, it is possible to associate several unique device IDs with a user (e.g., if a user has multiple devices). Participating devices can contribute interaction information in several ways. In a unilateral way, for example, the device senses information about its local environment, which may not require engaging in any of the peer-to-peer communication protocols described in the present disclosure. In a bilateral way, for example, the device communicates with nearby devices which are participating in this system. The collected information can be transmitted to a central authority, retained on the device, shared among a decentralized collection of devices, shared with nearby devices to assist with computation, or any combination. In some implementations, the information is collected automatically based on the device's physical activity and proximity to other devices. In some implementations, supplementary unilateral and bilateral interaction information can be contributed through other means, for example by having a user enter or scan a code (for example, a quick response (QR) code), or perform some action to indicate that they have regular direct or indirect contact with everyone else entering the same code (e.g., corresponding to an elementary school classroom). As an example, in implementations of using devices in elementary classrooms, parents can enter or scan a code corresponding to their kids' classroom, and users can be connected to everyone else who entered the same code. This may be necessary if kids/students are not carrying mobile devices (e.g., smartphones).

Unilateral Contribution

Some implementations of the system in this disclosure include the unilateral approach because it is sometimes more robust to running in the background on certain mobile operating systems, although the tradeoff is that less accurate information is recorded. Unilateral data collection also supports implementations where, for example, it is desirable to link two users if they were in the same approximate location during non-overlapping time windows, but where the time windows are not too far apart (e.g., in application contexts where an infected person contaminates a location for some time, departs, and then a second person visits the location). In an example of a unilateral approach, a participating device periodically wakes up (even if running in the background) and records sensor information about its environment. Some examples of the recorded information include: the current time, the lapsed time since the last unilateral scan, measurements from a proximity sensor or ambient light detector (for example, helping to indicate whether the device is in a pocket or purse), a device manufacturer and model, and operating system version, and an application (app) version. Recorded information can also include information about the wireless local area network (WLAN) access point currently connected to. Some examples include the basic service set identifiers (BSSID), service set identifier (SSID), received signal strength indicator (RSSI), and transmission power. Other recorded information can include: similar information about nearby WLAN access points; information about nearby BLUETOOTH devices such as media access control (MAC) addresses, RSSI, and transmission power; location information including latitude, longitude, and elevation, as collected from GPS or other absolute location sensors; and an identifier of a location defined by a scan of a posted quick response (QR) code, or a touch of a Near-Field Communication (NFC) enabled device.

In some implementations in which further privacy is desired, the following procedure can be applied to any sensitive information collected using, for example, wireless local area network (WLAN), BSSID+SSID, BLUETOOTH MAC address, or latitude+longitude+elevation). The time can be divided into predetermined intervals (e.g., every 15 minutes). Then, any sensitive information is combined with an identifier for the current time interval and passed through a deterministic hash function. The hash function can be selected to be computationally intractable to reverse. For example, if a nearby BLUETOOTH MAC address of 91:82:73:06:55:46 was observed on Jun. 14, 2020, at 16:52 UTC, and time was divided into 15-minute intervals, then the string "2020-06-14T16:45-91:82:73:06:55:46" could be passed through the hash function and recorded.

The benefit of this procedure is that hashes cannot be easily reversed, but if two hashes match, then two devices were in the vicinity of the same BLUETOOTH MAC address at some point in the same 15-minute interval. For greater robustness, this may also be done with other nearby 15-minute time intervals (e.g., also hashing "2020-06-14T17:00-91:82:73:06:55:46"). That way, two devices would still have a hash match if, e.g., one was near the BLUETOOTH MAC address at 16:52 and the other was near the address at 17:02.

In the case of latitude+longitude+elevation, the space of 3-dimensional GPS coordinates can first be partitioned into regions in a manner similar to how time was separated into intervals. Then, for each nearby region and each nearby time interval, the region identifier can be combined with the time interval identifier, passed through the hash function, and recorded.

For an alternative implementation to protect privacy, it is also possible for a separate server to maintain an ephemeral table associating WLAN information (e.g., derived from BSSID and/or SSID) or GPS regions with random tokens. The random tokens can be rotated on a predetermined schedule (e.g., every 30 minutes), always keeping track of both the current token and the preceding token, to help identify overlaps near the time of token rotation. Only the association between the random tokens and the user ID is persisted in long term storage. The association between WLAN or GPS information and the random tokens is not persisted in long term storage. As a result, if the database were someday compromised, it would be very difficult for an attacker to use the database to deduce the raw WLAN or GPS information of a user. Since a particular WLAN access point typically broadcasts several BSSID's, it is possible that this separate server uses separate information about which BSSID's are located near each other in order to determine which random token to return.

Bilateral Contribution

In the bilateral mode, participating devices communicate with each other and estimate the relative proximity between certain pairs (or groups) of devices. Proximity can be specified quantitatively as a physical distance estimate, or can be measured on an alternative scale, such as a signal-to-noise ratio of an audio (e.g., ultrasonic) or radio frequency (e.g., BLUETOOTH, ULTRA-WIDEBAND, etc.) pulse transmitted by one of the devices. Throughout this disclosure, BLUETOOTH will be used as a key example, but other radio frequency communication methods such as ULTRA-WIDEBAND can be used instead, or in addition, even if not explicitly mentioned. Multiple modes of proximity description can be specified. In some implementations, sending audio signals includes sending a "melody" of individual frequencies optimized for physical distance measurement between devices at rest, with characteristics that help to detect devices through sound-attenuating obstacles.

As a device communicates with another one (or a group), instead of transmitting its unique ID, the device can transmit an "alter ego" that is periodically regenerated. The device can communicate the correspondence between its true unique ID and its list of alter egos to the central authority.

In an example implementation, a participating device can periodically wake up (on a predetermined or random schedule) and use a short-range communication method (e.g., radio frequency, ultrasound, etc.) to scan the vicinity for nearby participating devices which are available to communicate. The communication protocol can be between pairs of devices or among small groups in a local vicinity. The devices can exchange alter egos, while also estimating their physical distances from each other, and each can record the interaction. When more than two devices are communicating in a small group, these estimates can be based on performing geometrical calculations from a set of measurements which may not be the full set of pairwise distances (e.g., using the triangle inequality to estimate the distance between Devices A and B based on measurements of their pairwise distances to Device C, or triangulation among more devices). In some implementations, the devices can also record other relevant measurements, such as the radio frequency received signal strength indicator and transmission power from the other device (which is well known in standard practice to be a method for roughly estimating proximity via the inverse-square law), or statistics from audio signal processing. In some implementations, the ultrasonic component of the protocol is not used at all, and distance estimates are made using radio frequency received signal strength indicators and transmission powers. A benefit of having all devices store records is to provide a defense against false interactions being injected into the system. For example, any false record of Device B interacting with Device A injected by a bad actor (Device B) would be missing the duplicate record made by Device A.

Natural and standard generalizations to coordinate multi-party communications are possible. An example implementation of a bilateral protocol based on BLUETOOTH Low Energy is as follows.

Device A initiates a vicinity scan to detect a list of devices advertising their presence. BLUETOOTH Low Energy communication returns information such as the received signal strength indicator and transmission power during this process that allows preliminary estimation of relative proximity to each device within detection range.

Device A successively connects to each of the nearby detected devices according to some order (e.g., based on communication signal strength, or estimated proximity, or device manufacturer as returned by the BLUETOOTH scan, or random).

FIG. 1A is a swim lane diagram showing an example of a dialogue 120 between a first device 122 (e.g., Device A) and a second device 124 (e.g., Device B) used in the present disclosure, according to some implementations of the present disclosure. When Device A connects with Device B, the following events can occur. At 126, Device A asks Device B for Device B's alter ego. At 128, Device B tells Device A that Device B will play a certain sound, often in the near-ultrasonic spectrum (18.5-19.5 KHz). At 130, Device A tells Device B that Device A will play a certain (often ultrasonic) sound. At 132 and 134, using their speakers and microphones (on board or via a connected peripheral, e.g., a wearable accessory), each device emits and captures the sounds that they emit as well as the sounds that the other devices emit. At 136, according to the Robust Ultrasonic Distance Ranging Protocol for Two Devices sections described in the present disclosure, Device A asks Device B for certain measurements from Device B's analysis of its own recording. At 137, Device B responds by sending measurements to Device A. At 138, according to the Robust Ultrasonic Distance Ranging Protocol For Two Devices, Device A analyzes its own recording, uses the measurements from Device B, and estimates the distance between them, or at least confirms whether Devices A and B are within ultrasonic transmission range. At 140, Device A sends information about the interaction to Device B, including the estimated distance (actual estimate returned by the Robust Ultrasonic Distance Ranging Protocol For Two Devices, or non-quantitative information that devices were within ultrasonic transmission range, or a distance estimate using Device A's measurement of Device B's BLUETOOTH signal strength and an estimate of Device B's BLUETOOTH signal transmission power, or non-quantitative information that devices were within BLUETOOTH Low Energy range but not within ultrasonic transmission range, or any combination of the above), Device A's alter ego, and the amount of time since Device A last performed a vicinity scan. Both devices record this information. In some implementations, devices also record additional information about this interaction that can be used to refine distance estimates (possibly after integration into a much larger dataset on the server side). Some examples include a device's measurement of the BLUETOOTH received signal strength indicator and estimated transmission power corresponding to the BLUETOOTH signal from the other device (which is well known in standard practice to produce a rough estimate of proximity via the inverse square law), or statistics from audio signal processing. Steps 128, 130, 132, 134, 136, 137, and 138 in FIG. 1A can be replaced by using other methods to estimate distances, such as using the BLUETOOTH received signal strength indicators. There can be multiple first devices and multiple second devices.

In order to conserve power, it is possible that Device A's connection with Device B may be cut short before it completes. It is also possible that Device A's successive connections to each of the nearby detected devices can be cut short after a timeout. The benefit of doing this is because in a large crowd, it may not be relevant to connect with all participating devices within BLUETOOTH range.

Measuring distance between devices can return a distance estimate, but in some adverse environments, the audio (e.g., ultrasonic) signal cannot be fully deciphered to produce an accurate distance estimate. As a fallback, the system relies on a more robust part of the audio ranging protocol which does not return a distance estimate, but returns a confirmation if the devices are able to hear each other. That is also already useful for contact tracing applications, making it possible to eliminate false positive detections through walls and ceilings.

In some implementations, the non-quantitative confirmation of whether or not the devices can hear each other is already useful enough. Indeed, due to the transmission characteristics of an airborne disease (e.g., COVID-19), being able to confirm whether two devices are in the same room (as opposed to being separated by walls or ceilings) already aligns with likelihood of transmission. Especially when paired with the early warning system later in this disclosure, it is already very useful if the audio step merely confirms that at least one device can hear the other.

Robust Audio Distance Ranging Protocol for Two Devices

The protocol of the present disclosure provides improvements over conventional techniques. The improvements include the ability to work in situations without a clear line-of-sight between the devices, and in noisy and reverberant environments. The protocol applies novel and non-trivial signal design (not only "chirp" or "Pseudo-random Noise (PN) signals") to achieve accuracy in these difficult environments. The signal design and processing are described in detail in this section, and empower the protocol to handle non-line-of-sight situations, while achieving accuracy with more efficient processing. Although this section focuses on audio signals, this signal design could be used for other types of signals and other frequency ranges as well. Descriptions of conventional systems may indicate, for example, that cross-correlation has a large computational cost. Also, signal design of the present disclosure is optimized for robustness to obstacles and noise, with particularly strong performance characteristics when both devices are at rest. The protocol still works when devices are moving, but the nature of contact tracing is such that it is especially valuable to be able to accurately estimate distance between at-rest devices, because that is how the devices often are during periods of extended human-to-human contact.

The protocol of the present disclosure introduces novel signal processing (not just "cross-correlation") which is more effective at reducing noise artifacts when analyzing signals with frequencies close to the Nyquist (upper) limit. This is particularly important for handling non-line-of-sight situations, because the shortest time-of-flight can correspond to a substantially attenuated signal that precedes a much more prominent echo. For example, if a thin obstacle attenuates the direct signal pathway, but there is a clear line-of-sight reflection off the ceiling, then the most prominent signal peak will correspond to the time-of-flight of the reflection off the ceiling, which may be far from the truth. In order to properly detect distance through the obstacle, it is then important to be able to sense the attenuated signal against the background noise. The signal design and processing of the present disclosure are better suited to handle this situation.

The short-range communication channel (established in the protocol in the previous section) allows the two devices to agree to start transmitting near-ultrasound audio imminently. Signals can be in the frequency range of, for example, 18.5-19.5 KHz because of limitations with smartphones from 2016-2020, which have uneven frequency response near and beyond 20 KHz, and because some people can hear beyond 18 KHz. The precise numbers are just a functioning example. Also, natural variations of the technique can be used in other implementations, such as playing repeated signals to increase accuracy.

Example Implementation of Audio Ranging Protocol

Figure 1B:
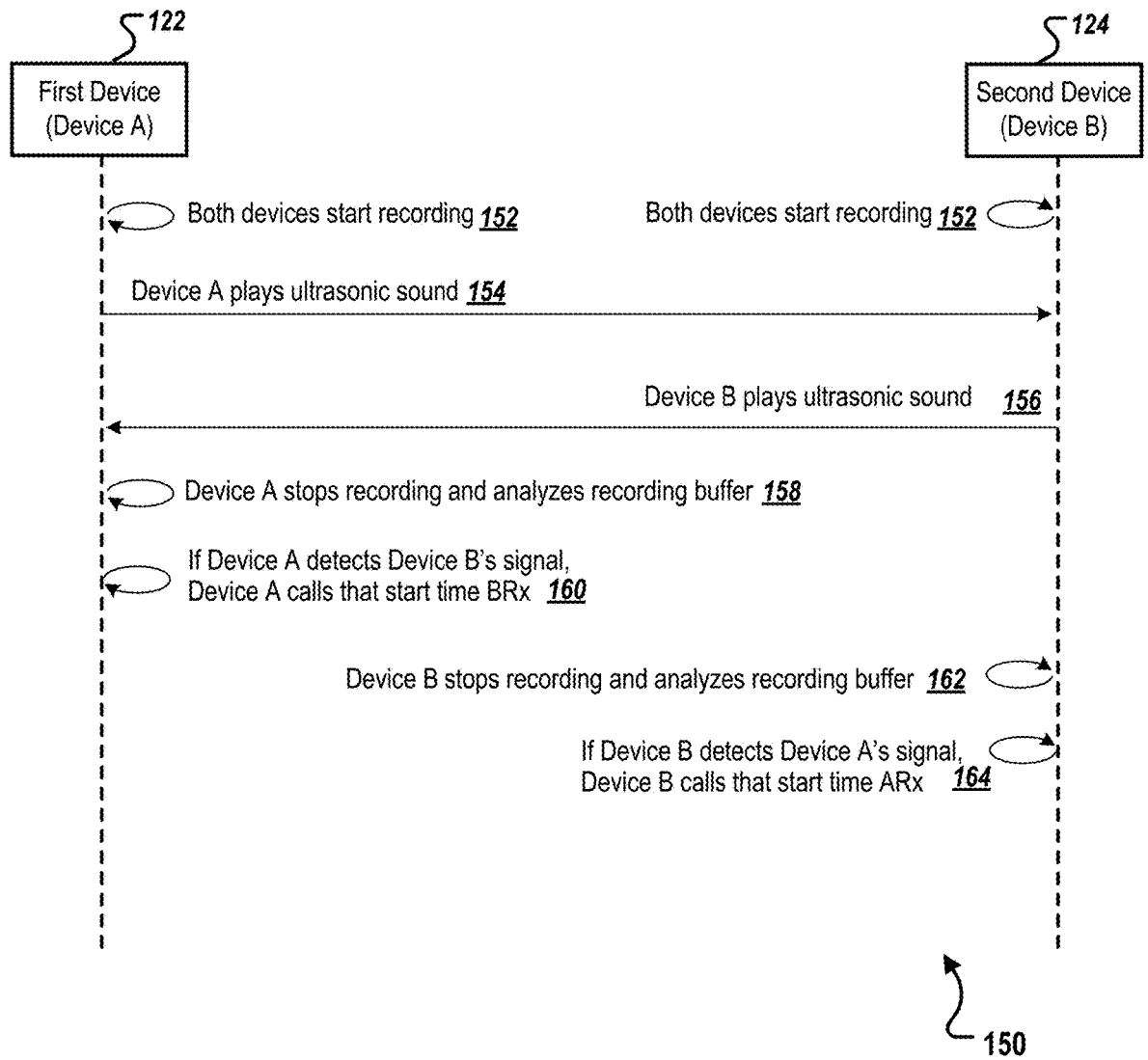
FIG. 1B is a swim lane diagram showing an example of a dialogue between a first device and a second device used in the present disclosure, according to some implementations of the present disclosure.

FIG. 1B is a swim lane diagram showing an example of a dialogue 150 between a first device 122 (e.g., Device A) and a second device 124 (e.g., Device B) used in the present disclosure, according to some implementations of the present disclosure. In an example implementation of Audio ranging protocol, both devices start recording at 152. At 154, Device A immediately plays an audio (e.g., ultrasonic) sound. For example, device A plays a buffer including a low-amplitude sine wave (to warm up output circuitry) for 500 milliseconds (ms) followed by its audio signal. This effectively makes its audio signal start playing in 500 ms. Concurrently, at 156, Device B immediately plays an audio sound. For example, device B plays a buffer including a low-amplitude sine wave (to warm up output circuitry) for 1500 ms followed by its audio signal. This effectively makes its audio signal start playing in 1500 ms.

At 158, e.g., at 2500 ms after starting to record, Device A stops recording and analyzes its 2500-ms-long recording buffer using the following steps. Device A searches for the start time of transmission of its audio signal within its recording buffer, and calls that start time ATx ("A-transmission"). All times corresponding to activity within a recording buffer are measured relative to the start of their recording buffer. Device A then searches for the start time of first receipt (in the event of echoes) of the audio signal from Device B within its recording buffer. Since the audio signal duration from Device A is known, Device A adds that duration to ATx, and searches the portion of its recording buffer from that point to the end. At 160, if Device A detects Device B's audio signal there, Device A calls that start time BRx ("B-receipt").

At 162, e.g., at 2500 ms after it starts recording, Device B stops recording and analyzes its 2500-ms-long recording buffer. Device B searches for the start time of transmission of its audio signal within its recording buffer, and calls that start time BTx ("B-transmission"). Note that this time is relative to the start of Device B's recording buffer. Device B then searches for the start time of first receipt (in the event of echoes) of the audio signal from Device A within its recording buffer. At 164, if Device B detects Device A's audio signal there, Device B calls that start time ARx ("A-receipt").

If neither one of ARx or BRx is defined (for example, neither device heard the other device's audio signal), this protocol concludes that the devices were not within audio transmission range. If only one of ARx or BRx is defined, the protocol can conclude that the devices were within audio transmission range (which can be defined to be 10 meters in an example implementation), but is unable to precisely determine their distance.

If both ARx and BRx are defined, then the average time of flight for the two audio signals is then estimated as: ((ARx−ATx)+(BRx−BTx))/2. This calculation is independent of the clock offset between when the two devices start recording, because the clock offset cancels. The distance can be estimated as the product of that time of flight and the speed of sound. If the estimate is negative or is larger than a threshold (e.g., 10 meters), the protocol can assume there was an error. The protocol can still conclude that the devices were within audio transmission range (e.g., 10 meters) and unable to precisely determine their distance. If the estimate is positive and is less than the threshold (e.g., 10 meters), then the protocol can return the distance estimate.

Communication Signal Design

In the current example, the communication signal transmitted by each device includes two parts: one of a preset collection of chromatic keys with a favorable autocorrelation profile which permits accurate detection of its start time, followed, for example, by a monotone sine wave or some other pre-defined wave. The chromatic keys are the result of careful signal design for challenging contact-tracing environments. In the audio signal context, one example implementation of a set of 10 chromatic keys includes the following. Three special frequencies are selected, for example, Frequency 0=18600 Hertz (Hz), Frequency 1=18900 Hz, and Frequency 2=19200 Hz. Ten carefully selected sequences of 60 numbers, each of which is 0, 1, or 2, are specified, with the following properties. For each particular sequence S (among the 10), and for every fixed positive integer D, there are at most 20 integers K such that the K-th term in the Sequence S equals the (K+D)-th term in the sequence S. For each pair of different sequences S and T (among the 10), and for every fixed nonzero integer D (positive or negative), there are at most 25 integers K such that the K-th term in the sequence S equals the (K+D)-th term in the sequence T.

For each of the 10 sequences, a discontinuous chromatic key is constructed that includes the melody where each of the 60 notes in the melody's sequence is played as a constant amplitude sine wave for a time interval of 1/300 second, according to the same sequence, while using the described correspondence between 0, 1, 2 and specific frequencies to determine which frequency plays for each time interval. The total length of the melody can be 200 ms, for example.

Each of the 10 discontinuous chromatic keys has a frequency(f)-vs-time(t) dependence f(t) which is a discontinuous piecewise-constant function with range {18600, 18900, 19200}. Since the discontinuity would create audible artifacts during speaker playback, the frequency-vs-time profile is smoothed and made into a continuous function g(t) by defining each desired instantaneous frequency g(t) to be the average of all f(u) in a window t−C<u<t+C for some preset constant value C (e.g., 0.0002 seconds). Use that resulting continuous g(t) to construct the chromatic key corresponding to that discontinuous chromatic key.

The rationale for the decisions in this particular example implementation include the following. The chromatic key system has particular additional benefits for devices at rest (with zero Doppler shift). When devices are moving, the chromatic key system can still be analyzed with Doppler corrections, but because a very substantial amount of contact-tracing impact is achieved by robustly detecting distances between devices at rest, the parameters are carefully chosen to provide additional performance benefits for that setting.

Smartphones typically use one of two sample rates: 48000 Hz and 44100 Hz. The greatest common divisor of 48000 and 44100 is 300, and so for either sample rate, a time interval of 1/300 second corresponds to an integer number of samples (160 samples or 147 samples).

Since each of the three special frequencies (18600, 18900, 19200) is a multiple of 300 Hz, each discontinuous chromatic key plays an exact integer number of cycles during each 1/300 second time interval corresponding to each of its 60 notes.

The low overlap between shifts of signals (including shifts of the same signal) corresponds to good cross-correlation and autocorrelation properties, with a distinctive autocorrelation peak of width approximately 1/300 second (the duration of holding one note in the melody). The numbers 20 and 25 above are not the best possible, but are achievable in a prototype, constructed by considering millions of random sequences and selecting the best ones that appeared.

In some implementations, even greater care will be taken to assure that for each 60-note sequence S, each note (0, 1, or 2) appears exactly 20 times. Also, for each note N in {0, 1, 2} and for each positive integer D, there are at most 8 integers K such that both the K-th and (K+D)-th notes in the sequence S are equal to N. Such a construction will yield even better mathematical characteristics during signal processing, and the particular numbers (60, 20, 8) correspond to what can feasibly be found by randomly trying sequences with 20 of each of {0, 1, 2}, since 8 is safely greater than 1/3 of 20.

This 1/300 second time scale for autocorrelation peak width is acceptable because the speed of sound is approximately 343 meters per second, and so the peak width corresponds to the time during which sound travels less than one meter. That level of accuracy is sufficient for contact tracing applications. For other applications, different parameters may be chosen.

This protocol is designed for challenging situations where line of sight may be obstructed. In order to detect the first receipt of a signal when the direct path arrives as a severely attenuated signal, followed by several stronger echoes, it is necessary that the peak width is narrow enough to resolve the attenuated first signal peak apart from the later echo peaks. In the common situations where echoes correspond to reflected paths that are at least a meter longer (e.g., up to the ceiling and back down again), the 1/300 second timescale is then sufficient for resolution, while still providing the integer-type characteristics (in each note time interval, integer numbers of samples and integer numbers of cycles) that will enable more efficient signal processing below.

A sample implementation then includes transmitting a communication signal having one of the 10 chromatic keys, followed by a 200 ms sine wave at a certain device-selected audio frequency (which is reasonably distinguishable from the 3 designated chromatic key frequencies, including not having too large of a common factor). While the communicating devices are negotiating the parameters of this Robust Audio Distance Ranging Protocol for Two Devices, each communicates which of the 10 chromatic keys it will send, followed by which specific constant frequency. (The 10 chromatic keys are specified in advance for all devices to use.)

In some applications, the chromatic key is not included in the communication signal, so as to provide a longer duration for the constant frequency. For example, there are some applications in which it is not necessary to accurately estimate the distance between devices, but rather where it is already useful to know that the two devices are close enough to be able to detect any sonic signal at all.

In some applications, the monotone frequency after the chromatic key is not included in the communication signal. For example, in some applications the chromatic key itself is enough, and it is beneficial not to use any transmission time on the monotone frequency.

Communication Signal Processing

This protocol's approach also uses sample counting within the recording buffer, dividing by the sample rate to achieve an estimate of time since the start of the recording buffer. The protocol applies a signal processing algorithm four times: twice in Device A's recording buffer, and twice in Device B's recording buffer. In the example implementation, each invocation of the algorithm is on a segment of the recording buffer, searching for a specified frequency F of specified duration D, preceded by a specific chromatic key, with the objective of determining exactly when this signal first started being heard in the recording buffer.

The reason for basing the construction on the piecewise constant-frequency discontinuous chromatic key is because it is particularly efficient to calculate the following. Given a fixed frequency G and duration of N samples, the algorithm determines, for all sample indices K in a buffer B with sample indices starting from 0, the Fourier coefficient magnitude (of a complex-number Fourier coefficient) corresponding to frequency G over the signal starting from sample index K, lasting for a duration of N samples. The analysis compares ratios of Fourier coefficients, and so normalization constants are ignored throughout this disclosure. One way to achieve this is to perform the following algorithm which has complexity that is linear in the number of samples in the buffer.

Example Single Frequency Correlation Contiguous Window Algorithm

A single frequency correlation contiguous window algorithm can be used, for example, to determine a Fourier coefficient magnitude corresponding to frequency G over the duration-N-samples signal starting from sample index K. The algorithm's inputs can include: Buffer B with sample indices starting from 0, Frequency G, and Duration N samples. The output includes determining, for all sample indices K in the buffer B, the Fourier coefficient magnitude (of a complex-number Fourier coefficient) corresponding to frequency G over the duration-N-samples signal starting from sample index K. The algorithm constructs a sine wave function S(J) corresponding to frequency G, defined over the same domain of sample indices as the buffer. Note that S(0)=0. The algorithm constructs a cosine wave function C(J) similarly. Note that C(0)=1. For each K, the algorithm calculates the running total (interpretable as partial sums, or integrals) of S(J)B(J) as J runs from 0 to K. For each K, the algorithm calculates the running total (interpretable as partial sums, or integrals) of C(J)B(J) as J runs from 0 to K. The algorithm subtracts pairs of running totals to calculate, for each K, the sum $S_K$ of S(J)B(J) over all K≤J<K+N, and also the sum $C_K$ for C(J)B(J). For each K, the corresponding Fourier coefficient magnitude (up to a constant normalization factor) is simply $\sqrt{(S_K^2+C_K^2)}$. Note that if there is zero Doppler shift, if the room is anechoic, and there is a single source of a single-frequency pulse for N samples, then by running the algorithm, the largest Fourier coefficient magnitude will correspond to a good estimate of the start of the pulse.

The next algorithm extends this simple observation to analyze the chromatic keys. Each chromatic key is a smoothed version of a discontinuous chromatic key, and the analysis considers how one can clearly detect a discontinuous chromatic key. Since these keys approximate each other, the signal processing method will also identify the chromatic key. The structure of a discontinuous chromatic key includes a few fixed frequencies (3 in the example implementation), played over a small number of disjoint intervals (60 in the example implementation). The lengths of the intervals and the frequencies have been selected so that when there is zero Doppler shift: each interval is an integer number of samples, and each interval contains an integer number of cycles of the monotone frequency being played over that interval.

Consequently, for each frequency in the discontinuous chromatic key, if one considers the part of the discontinuous chromatic key corresponding to that particular frequency, it completes integral numbers of cycles over each disjoint interval on which it is playing, and if the rest of the domain were erased, and these disjoint intervals were spliced together, the signal would be a perfect sine wave over a domain of length equal to the total length of those intervals.

Importantly, there is no phase mismatch as the wave finishes one interval and starts the next, even if they were originally separated by several other notes corresponding to other frequencies. This is why it is valuable to have integral numbers of cycles finishing over intervals that were integral numbers of samples. So, from the perspective of Fourier analysis, each of the few frequencies in the discontinuous chromatic key is just a single sine wave supported on a single long interval created by discarding the other notes and splicing the individual intervals together.

This interpretation confers significant benefits in terms of computational efficiency and robustness to noise, including noise produced by multipath reflections (which would be in the same frequency range). Specifically, the signal-to-noise ratio corresponding to each particular frequency's Fourier coefficient is comparable to what one would detect if instead of the chromatic key, one simply played the first frequency for its total duration (in the key), then the second frequency for its total duration, and then the third frequency for its total duration (if there were 3 frequencies). Yet, that alternative signal design would have poor autocorrelation properties. So, the signal design acquires the signal-to-noise robustness of a long-duration single-frequency sine wave while simultaneously enjoying the precise autocorrelation benefits of a chirp or pseudorandom noise signal.

In contrast, if the magnitudes of the (complex number) Fourier coefficients are computed corresponding to each single frequency over its short interval (1/300 second in the example), and the values are averaged, the result would be less robust to noise. That is because over each short interval, noise could contribute to a small-magnitude Fourier coefficient, but with random complex argument. Without alignment of the phases over different intervals, it would be unclear how to combine these Fourier coefficients. A simple average of the magnitudes could potentially just be noise. The technique essentially averages the Fourier coefficients as complex numbers (not just as nonnegative real number magnitudes), thereby averaging out noise effects that cancel out as complex arguments are taken into account.

Also, due to the integrality throughout the signal construction, it is computationally very efficient to calculate the magnitude of the Fourier coefficient corresponding to each frequency F in the discontinuous chromatic key. If there is zero Doppler shift, if one simply creates a single frequency-F sine wave signal S(J) of the same length as the recording buffer, then wherever the discontinuous chromatic key is played (even if it starts at a time corresponding to a non-integral sample in the recording buffer), the frequency-F portions of the discontinuous chromatic key will always have the same relative phase with S(J). The same is true for a frequency-F cosine signal C(J).

Even if there is a known nonzero Doppler shift, so that the transmitted frequency F is received as a frequency G, then if one simply creates a S(J) and C(J) corresponding to frequency G instead, then the originally-frequency-F portions of the discontinuous chromatic key are recorded as frequency-G intervals, and the signal in those frequency-G intervals also always has the same relative phase with S(J) and C(J). In this way, the relative phase remains constant even across separated intervals within the Doppler-shifted discontinuous chromatic key, which makes it possible to achieve robust detection against noise by combining the Fourier coefficients over different intervals as full complex numbers instead of just magnitudes. This all enables the following algorithm, which also runs in time linear in the buffer length.

Single Frequency Correlation Separated Windows Algorithm

A single frequency correlation separated windows algorithm can be used, for example, to determine, for all sample indices K in a buffer B, a Fourier coefficient magnitude (of a complex-number Fourier coefficient) corresponding to a frequency G. The Fourier coefficient magnitude can be calculated over a collection of disjoint intervals corresponding to indices of intervals in the input, relative to a starting sample index of K. The algorithm's inputs include: Buffer B with sample indices starting from 0, Frequency G to search for in buffer (corresponding to 18600, 18900, or 19200 in the sample if there is zero Doppler shift, but different if there is a Doppler shift), a number of samples N in a single-note interval (corresponding to 160 at 48 KHz sample rate in the example if there is zero Doppler shift, but possibly non-integral if a nonzero Doppler shift compresses or extends the interval), and a set of indices of intervals in the discontinuous chromatic key with frequency G (subset of {0, 1, 2, . . . , 59} in the example). The output can include determining, for all sample indices K in the buffer B, the Fourier coefficient magnitude (of a complex-number Fourier coefficient) corresponding to frequency G over the collection of disjoint intervals corresponding to the indices of intervals in the input, relative to a starting sample index of K. In the example, if the indices were {0, 2, 59} and N is integral, then the domain would be the union of sample indices [K, K+N)∪[K+2N, K+3N)∪[K+59N, K+60N), and just as explained above, the Fourier coefficient would correspond to what would be calculated if these intervals were spliced together into a single interval of 3N samples.

The algorithm (written for integer N, with rounding adjustments for non-integer N) constructs a sine wave function S(J) corresponding to frequency G, defined over the same domain of sample indices as the buffer. Note that S(0)=0. The algorithm constructs a cosine wave function C(J) similarly. Note that C(0)=1. For each K, the algorithm calculates the running total (interpretable as partial sums, or integrals) of S(J)B(J) as J runs from 0 to K. For each K, the algorithm calculates the running total (interpretable as partial sums, or integrals) of C(J)B(J) as J runs from 0 to K. The algorithm subtracts pairs of running totals to calculate, for each L, the sum $S_L$ of S(J)B(J) over all L≤J<L+N, and also the sum $C_L$ for C(J)B(J). Define the complex Fourier coefficient corresponding to this part as $Z_L = C_L + i S_L$. For each K, the algorithm adds together (as complex numbers) the $Z_L$ corresponding to the set of indices of intervals in the input. For example, if the set of indices was {0, 2, 59}, one would add together $Z_K + Z_{K+2N} + Z_{K+59N}$. The magnitude of this sum as a complex number will be the output value corresponding to K. In the example, since there are only 60 intervals in the discontinuous chromatic key, this corresponds to at most 60 operations for each K.

Now that the Single Frequency Correlation Separated Windows Algorithm has fully stated, the different analyses can be combined for the individual frequencies in the chromatic key. Although the algorithm is stated in terms of the discontinuous chromatic key, its output is reasonably good even if the buffer contains a (smoothed) chromatic key, because the two signals approximate each other.

Example Chromatic Key Signal Detection Algorithm

A chromatic key signal detection algorithm can be used, for example, to determine, for all sample indices K in the buffer B, a nonnegative real number score. Higher scores can indicate a greater confidence that a chromatic key is present, starting at sample index K.

The algorithm's inputs include: Buffer B with sample indices starting from 0, a True (non-Doppler-shifted) transmission duration of a note in discontinuous chromatic key, a Sequence of notes (true non-Doppler-shifted transmission frequencies) in Discontinuous chromatic key, and a Doppler shift factor. Outputs include determining, for all sample indices K in the buffer B, a nonnegative real number score, where higher scores indicate greater confidence that a chromatic key is present, starting at sample index K.

For each frequency F in the discontinuous chromatic key, the algorithm conducts the Single Frequency Correlation Separated Windows Algorithm on that frequency F (with parameters Doppler shifted). Receive for each sample index K, the magnitude of the complex Fourier coefficient corresponding to frequency F, and call it $M_K^F$. For each sample index K, there are now several nonnegative real numbers $M_K^F$. (In the example, there are 3 such numbers.) For each sample index K, the algorithm multiplies these numbers together, and let that be the nonnegative real number score corresponding to K. In some implementations, alternative functions (as opposed to the product) may be used to combine the nonnegative real numbers $M_K^F$ in the final step. For example, the sum could be used.

One potential benefit of using the algorithm is that from a pure Fourier-analytic perspective, each $M_K^F$ actually corresponds to the complex number magnitude of a bona fide Fourier coefficient. Since the discontinuous chromatic key was intentionally constructed with low autocorrelation (every relative shift of a signal with itself has less than about ⅓ of the notes matching in the example implementation), one would expect that for each fixed frequency F in the discontinuous chromatic key, the plot of the magnitude $M_K^F$ itself has a narrow peak near the K corresponding to the true start of the key (with 3 times the height of all other peaks).

The particular application seeks to detect an attenuated signal through an obstacle, even if there is a more prominent detected peak from a multipath reflection, specifically seeking to identify weaker peaks. The several frequencies (3 in the example) then work to an advantage, as they provide separate sources of confirmation of a possible peak. This motivates taking the AND of the possible peak detections, which is analogous to taking a product instead of a sum. Indeed, with a sum (which is analogous to an OR), it is possible for one frequency's Fourier coefficient magnitude to be uncharacteristically large and carry the sum, while the other frequencies have Fourier coefficients near zero. With the product, it only takes one frequency to have Fourier coefficient near-zero to drag down the product.

It is worth briefly comparing the algorithm against a standard discrete matched filter. The algorithm is not only more computationally efficient, but it also produces a score graph which is much smoother than the output of the matched filter, especially in the setting where the signal frequencies are necessarily close to the Nyquist frequency (ordinary smartphones are being used, while attempting to use the small amount of headroom between the threshold of human hearing and the speaker/microphone capability). Indeed, in that setting near the Nyquist frequency, even a +0.5 sample index difference corresponds to a substantial change in the signal, because half a sample index may be near a quarter wavelength. And, the integral of (sin x)(sin x) is noticeably positive, whereas the integral of (sin x)(cos x) (with a quarter wavelength shift) is essentially zero. The matched filter takes the inner product of the recording buffer against shifts of one signal, taking strides of +1 sample at a time (which are huge because the frequencies are close to Nyquist). Consequently, these inner products rapidly oscillate around 0, creating a situation where their absolute values produce a graph with many extremely narrow peaks.

One could smooth out this graph by applying several matched filters in parallel, corresponding to slight time-delays of the target signal by 0.1 sample index, 0.2 sample index, etc. Then, their pointwise maximum value would eliminate the artifacts from working too close to Nyquist, but this would be computationally heavy.

The chromatic key design allows us to achieve the smoothed result in one shot by leveraging the orthogonality of (sin x) and (cos x). Instead of needing to take a pointwise maximum of several inner products against fractional shifts of the target signal, the inner product with sine and the inner product with cosine are enough, combined via the Pythagorean formula. The score graph is then smooth, and each peak has a clear artifact-free form. Consequently, when the sample index is found which corresponds to the maximum height of a peak in the score graph, it is a more accurate estimate of the true signal start time than, say, interpolating an envelope of narrow maxima from the output of a rapidly-oscillating matched filter.

Furthermore, the chromatic key enables us to produce several independent sources of peaks, which can be ANDed to detect an attenuated peak that may precede the highest peak (due to an otherwise-unobstructed multipath reflection). The mathematical properties of the example chromatic key make the true peak for each frequency approximately 3 times as high as any nearby autocorrelation peak for that frequency, and so after taking the product in the algorithm, any peak can be expected to be safely 27 times as high as nearby autocorrelation peaks. (This appears in experimental results as well.) This mathematical control proves to be useful in identifying attenuated peaks.

Example Full Audio Signal Processing Algorithm

An audio (e.g., ultrasonic) signal processing algorithm can be used, for example, to determine a time relative to a start of a buffer at which a chromatic key is estimated to start. The algorithm's inputs include: Buffer B, a True (non-Doppler-shifted) transmission duration of a note in discontinuous chromatic key, a sequence of notes (non-Doppler-shifted transmission frequencies) in discontinuous chromatic key, a true transmission frequency F and true transmission duration D of constant-frequency pulse (if any) following a chromatic key, and a Doppler shift tolerance (e.g., up to Doppler shifts corresponding to relative velocity of up to ±1 meter per second which is sufficient for contact tracing applications). Outputs include determining a time relative to start of buffer at which chromatic key is estimated to start.

The algorithm searches for a duration D constant-frequency pulse at the expected frequency F, allowing for Doppler shifts up to the given tolerance. One way to accomplish this is to use the Single Frequency Correlation Contiguous Window Algorithm to compute all Fourier coefficient magnitudes corresponding to frequency F for the duration D, starting at all possible indices.

Since the allowed Doppler shift is quite small (corresponding to around 50 Hz if F=19 KHz), the index I yielding the largest magnitude will likely be near where frequency F begins. In some implementations, several other such indices I can be considered which are widely separated from each other, but have relatively high magnitude.

A Fourier transform is performed in that vicinity. If there is no uniquely prominent peak Fourier coefficient magnitude in the frequency spectrum near frequency F, up to the given Doppler shift tolerance, the algorithm is completely aborted, as even the constant-frequency pulse was not heard.

If there is a uniquely prominent peak Fourier coefficient magnitude at frequency G, but G is within some very small tolerance of F, it can be assumed that there is zero Doppler shift. In some implementations, if there are a few prominent peaks, the algorithm can consider them as possibilities as well. In some implementations, the algorithm does not perform such thresholding near zero, and can use any Doppler shift, however small.

Otherwise, it is assumed that the Doppler shift corresponds to the change in frequency from F to G. In this case, initial steps of the algorithm are repeated, and frequency G is used instead to find the largest Fourier coefficient magnitude corresponding to frequency G for the duration D. The rest of the algorithm can be interpreted as if all frequencies are shifted by this same Doppler correction.

Regardless of whether or not a uniquely prominent peak Fourier coefficient magnitude exists at frequency G, as long as the algorithm was not aborted, a rough estimate exists of when the constant-frequency pulse started. Assuming that the constant-frequency pulse was detected (and the protocol not aborted), attention can be turned to determining the start of the chromatic key.

The algorithm can optionally perform other signal processing methods on the constant-frequency part to provide alternative estimates of the start of the chromatic key. For example, in many instances the graph of the Fourier magnitudes produced by the Single Frequency Correlation Contiguous Window Algorithm has a distinctive shape which is near-0 until the vicinity of the pulse, upon which the graph rises linearly at a steady slope to a peak, and then falls at the same slope from the peak back to near-0. Analysis of this graph (e.g., fitting a straight line to the buildup towards peak and intersecting it with the horizontal axis) can also produce a rough estimate of where the constant-frequency pulse starts.

Taking into account estimates of where the constant-frequency pulse might start, a region of the buffer is defined in which to search for the chromatic key. The chromatic key Signal Detection Algorithm is conducted in that region to compute scores for every sample index in that region, and to detect the highest peak (score).

From that highest peak, the algorithm can search for an earlier attenuated peak (score) nearby, in case there was a shorter pathway for the sound to travel. This can be done by passing through a sound-attenuating object, or reflecting off a non-optimal surface or oddly-shaped object, while the strongest signal may have reflected off the flat but faraway ceiling. Note that conducting the Chromatic Key Signal Detection Algorithm in that region already computed scores for all sample indices in this region.

A range R of indices to search is defined as follows. The first sample index to consider is set to be some number of samples earlier than the sample index of the highest peak. For example, that number of samples could correspond to the amount of time it takes sound to travel about 20 meters. As such, the contact tracing application may look back this far because the difference in length between a direct path and an indirect reflected path via the ceiling is a few meters. Other implementations may choose different values. The last sample index to consider is set to be the sample index of the peak when conducting the Chromatic Key Signal Detection Algorithm.

A noise floor is defined to be that peak score, divided by a constant factor defined by the mathematical autocorrelation characteristics of the chromatic key (in the example, this is 27). If there are scores near the first sample index in the range R that are greater than the noise floor, the noise floor is increased to be equal to the maximum score seen here. A threshold T is defined for a peak to count (e.g., 3 times the noise floor, in the example implementation). The algorithm searches for peaks in the scores corresponding to indices in the range R. The algorithm can take the first peak that is found which exceeds the threshold T, and return that index as the start of the chromatic key, converted into a time since the start of the buffer. If no such peak is found, the original peak index is returned as the start of the chromatic key, converted into a time since the start of the buffer.

Alternative implementations can include the following. In applications where no constant-frequency pulse is transmitted during a communication period (for example, a few seconds or another configurable threshold time period), note that the Doppler shift can already be estimated using a previously-described procedure applied to just one frequency within the chromatic key. (This may be done for several chromatic key frequencies individually as well.) Indeed, in the example implementation there are only 3 frequencies in the chromatic key, and the distribution of, say, the notes corresponding to "frequency 0 (18600 Hz)" were originally scattered across the 60 possible notes in a random-looking pattern consuming about ⅓ of the chromatic key duration. So, executing the previously-described procedure applied with just 18600 Hz and a duration equal to the full chromatic key duration would still detect the approximate region containing the chromatic key. A Fourier transform there would surface 3 frequencies (the Doppler-shifted versions of 18600 Hz, 18900 Hz, and 19200 Hz), and the Doppler shift can be estimated from there.

It is also possible to use other methods to estimate the region of interest to search for the chromatic key. For example, one can use a matched filter to search the entirety of buffer B for several different Doppler shifts of the entire transmitted signal (chromatic key plus constant-frequency pulse).

The algorithm can benefit from having a non-noisy chromatic key score graph, because the graph avoids the aforementioned many repeated narrow peaks that appear as discrete match filter artifacts when working with signals near the Nyquist frequency. It then becomes possible to reliably identify significantly attenuated peaks. For reference, in conventional systems, earlier peaks may be detected if they are some very large fraction (for example, 85%) of the highest peak.

In contrast, in experimental results with the chromatic key, earlier attenuated peaks are correctly detectable even in situations where the earlier peak has a score that is only about 10% as high as the highest peak score. This is because there are no noisy artifacts from discrete sampling, and experiments confirm that the nearby autocorrelation peaks corresponding to the highest peak score indeed do not exceed their theoretical fraction of 1/27 (approximately 3.7%) of the peak height. The reason why a noise floor is estimated is because peaks are well-defined without significant noisy artifacts. Also, it is safe to identify (possibly very significantly attenuated) peaks based on their rise above the noise floor, instead of purely as a fraction of the highest peak height. This enables the chromatic key approach to detect severely attenuated peaks, even in environments with ambient noise.

Aggregation Framework

Figure 1C:
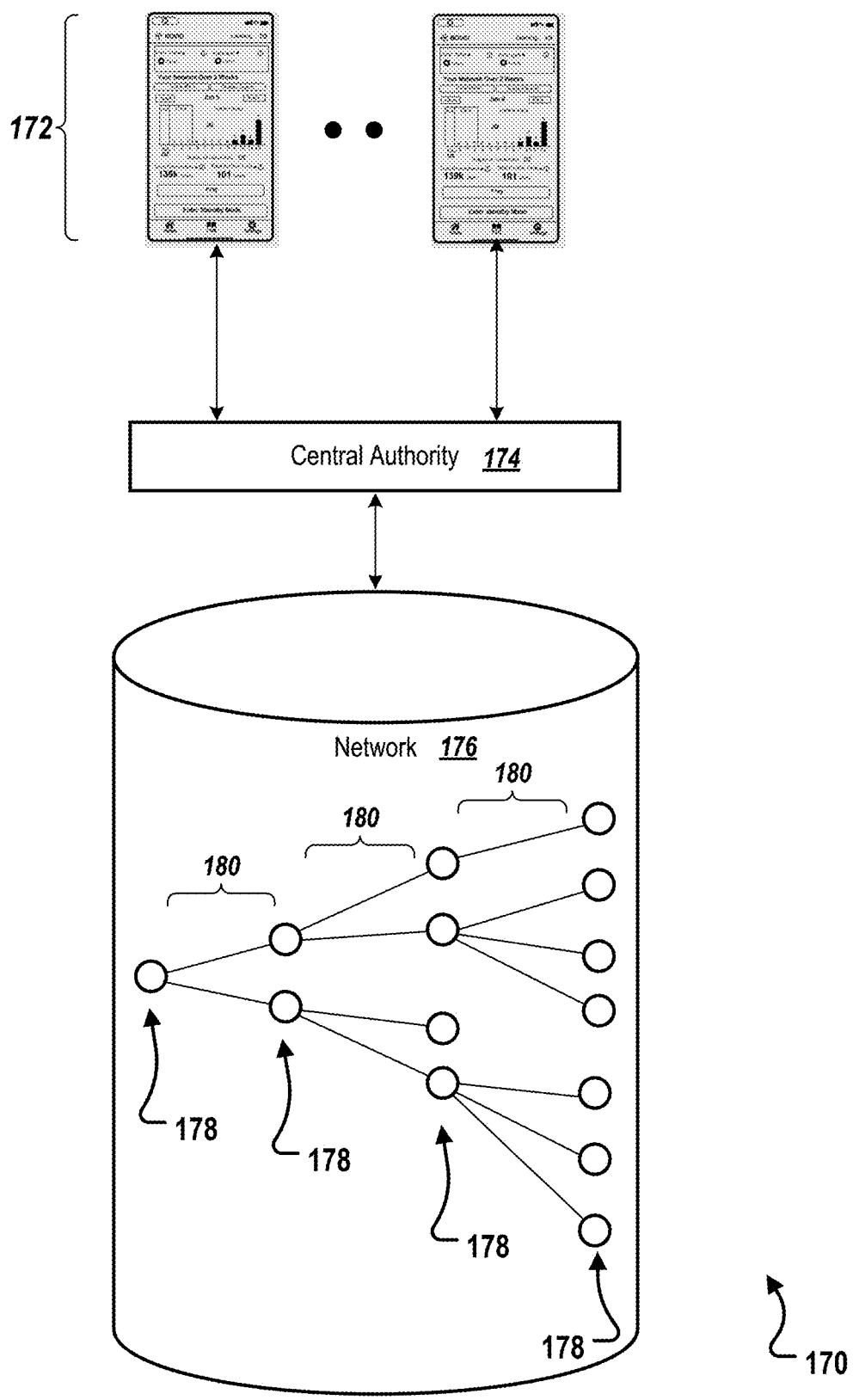
FIG. 1C is a block diagram showing an example of a system for recording and storing transactions, according to some implementations of the present disclosure.

FIG. 1C is a block diagram showing an example of a system 170 for recording and storing transactions, according to some implementations of the present disclosure. Electronic communication devices 172 (e.g., mobile electronic communication devices) in the system 170 can record information (e.g., through unilateral contributions or bilateral contributions as disclosed herein) that can be used by a central authority 174 to construct/reconstruct a network 176 of user-to-user close-physical-proximity interactions based on device-to-device close-physical-proximity interactions and device-to-user relationships. This can be done by the central authority 174 or can be constructed in parts in a decentralized or peer-to-peer fashion. This section will describe an example where the central authority 174 receives all information recorded by the mobile devices 172. Natural adaptations to decentralized or peer-to-peer implementations are permissible, in which electronic communication devices possess partial information about the network. Indeed, for the purpose of showing each user information about their network within a particular network-distance (e.g., 12) away, it is enough for electronic communication devices to work with partial network information corresponding to other devices within network-distance (e.g.) 12, and it is not required for the whole network to be centrally stored in order to compute that information. Although the network 176 is depicted as a tree structure, edges 180 can also occur in the network 176 between nodes of any layers of the depicted tree (including within the same layer), and nodes may have multiple edges connecting them to different nodes in any other layer.

The array of electronic communication devices 172 periodically sends observed interaction records (unilateral and bilateral) to the central authority 174 operated, e.g., by one or more server devices. Data can also (or alternatively) be sent to a decentralized infrastructure. The observed interaction records can include information such as positions/locations of the electronic communication devices, distance to another electronic communication device, and status signals, such as whether a user of the device has reported a specified status signal (e.g., positivity, being a contact-traced contact, symptoms, vaccination status, etc.). When outside of Internet connectivity, an electronic communication device 172 continues recording interactions, because even their bilateral interactions are collected using short-range communication protocols that do not require the Internet; the electronic communication device 172 then uploads all not-yet-uploaded interactions to the central authority once the device 172 has Internet connectivity.

Based on the information received from the electronic communication devices, the central authority 174 constructs one or more networks 176 that represent pairwise interactions between users, with respect to certain natural parameter sets. In some implementations, the nodes in a network 176 correspond to distinct users (described in this example for simplicity). Also (or alternatively), partial networks 176 can be constructed by a decentralized infrastructure (it is possible to decentralize using partial networks when delivering user interface elements which are computed using information from other nodes within some given network-distance away). In some implementations, the nodes correspond to distinct users, where several devices may correspond to the same user, and any interaction with one of the user's devices is considered to be an interaction with the user. In some implementations, there are no users, and the entire system operates as if each device is a distinct user. The networks 176 can include contact proximity networks that identify a network distance between and among nodes of the network. The contact proximity networks can be used to monitor status signals across the contact proximity network and, e.g., trace a spread of a specified feature through the contact proximity network.

A non-exclusive list of some examples of such networks 176 include the following. In one example, two users, e.g., User A (a node 178) and User B (a node 178) have an edge 180 between them precisely when, between Jun. 14, 2020 at 00:00 UTC and Jun. 21, 2020 at 00:00 UTC, there was a total of at least 15 minutes during which Users A and B had devices which detected that they were within 2 meters of each other. Users 172 are represented as nodes in the network 176.

In another example, User A (node) and User B (node) have an edge between them precisely when, between Jun. 14, 2020 at 00:00 UTC and Jun. 21, 2020 at 00:00 UTC, there was a total of at least 15 minutes during which Users A and B had devices which detected that they were within 10 meters of each other or within audio transmission range.

In another example, User A (node) and User B (node) have an edge between them precisely when, between Jun. 14, 2020 at 00:00 UTC and Jun. 21, 2020 at 00:00 UTC, there were at least 2 different times, separated by at least 5 minutes, such that at those times, Users A and B had devices which detected that they were within short-range communication range (e.g., detected each other via the Example Implementation of BLUETOOTH Low Energy Bilateral Protocol).

In another example, User A (node) and User B (node) have an edge between them precisely when, between Jun. 14, 2020 at 00:00 UTC and Jun. 21, 2020 at 00:00 UTC, at least one of the following conditions is true. There are least 2 different times, separated by at least 5 minutes, at which Users A and B had devices which detected that they were within 10 meters or within audio transmission range. Or there are at least 2 different 15-minute intervals, separated by at least 1 hour, where Users A and B had devices which detected that they both were connected to the same WiFi access point within those 15-minute time intervals.

In another example, User A (node) and User B (node) have an edge between them precisely when, between Jun. 14, 2020 at 00:00 UTC and Jun. 21, 2020 at 00:00 UTC, there are at least 2 different 15-minute intervals, separated by at least 1 hour, where Users A and B had devices which both detected the same BLUETOOTH MAC address in their vicinity during the 15-minute interval.

In another example, User A (node) and User B (node) have an edge between them precisely when, between Jun. 14, 2020 at 00:00 UTC and Jun. 21, 2020 at 00:00 UTC, there are at least 2 different 15-minute intervals, separated by at least 1 hour, where Users A and B had devices which detected that they were both within the same GPS latitude/longitude/elevation bucket in those 15-minute intervals.

In another example, User A (node) and User B (node) have an edge between them precisely when, between Jun. 14, 2020 at 00:00 UTC and Jun. 21, 2020 at 00:00 UTC, there is at least one GPS latitude/longitude/elevation bucket in which both Users A and B had devices present for at least 1 hour, and either their time windows of presence overlap, or their time windows are separated by less than 2 hours of gap during which neither of Users A nor B were present in that GPS bucket. This is an example implementation of a relative physical space and time proximity criterion, because it corresponds to approximately the same spatial location at approximately the same time. In some implementations which involve non-overlapping time windows of presence, some edges of the contact proximity network are directed, representing one-way directions of transmission (e.g., if User A visits a location before User B, then that could correspond to disease transmission from User A to User B, but not vice versa). The methods in this disclosure generalize naturally to directed networks, even when they are described for undirected networks in this disclosure.

The networks can be constructed and stored (in centralized or decentralized infrastructure) using the interaction data supplied from the mobile devices, with at least two possibly nontrivial steps. The following two sections describe example implementations of those two steps.

Determining Interaction Duration

In some example implementations, electronic communication devices do not directly record the duration of each interaction, in order to save battery. Instead, the electronic communication devices record snapshots of what they detect at particular intervals. The electronic communication devices also record the amount of time that has passed between their successive snapshots. These numbers can be used to estimate the total duration of time Devices A and B spent, for example, within 2 meters over a fixed time window, as follows.

The estimation can begin by searching for bilateral interactions recorded where Device A initiated the vicinity scan of the example BLUETOOTH Low Energy bilateral protocol, in which Device B was detected at a distance within 2 meters. Each such interaction includes metadata of how much time has elapsed between the vicinity scan and the previous time that Device A initiated a vicinity scan. In some implementations, a sum of such elapsed times (possibly including using thresholding to truncate a value if it is unusually large) can be computed to determine an estimate from Device A's perspective of how much time Device B was within the requisite distance.

The steps can be re-performed with the roles of Devices A and B reversed, to determine an estimate from Device B's perspective of how much time Device A was within the requisite distance. The maximum of the estimates can be returned as the desired duration estimate.

The reason for calculating the maximum of the two duration estimates is because, although in an idealized situation, each of the estimates is independently accurate, in the real world sometimes devices fail to detect each other. For example, in some cases, a certain Device A may consistently have issues initiating vicinity scans, and the maximum calculation allows the other Device B to supply the interaction duration estimate. In some implementations, devices may scan continuously or have other methods of determining continuous interaction duration directly, in which case this computation is then unnecessary.

Matching Unilateral Detections

As mentioned previously regarding collecting unilateral interactions, some implementations can preserve privacy by deterministically hashing raw information (e.g., WLAN information) together with a 15-minute time interval identifier. The nature of the hashing is such that for of the example network constructions previously described, the hashes can be compared directly for exact matches, with no need to reverse the hashes.

Status Signal Collection Subsystem

A central authority or decentralized infrastructure can collect status signals from various sources associated with users. These status signals can then be processed, and information can be associated with users in the system. In some implementations, there are trusted users who can confirm the authenticity of the status signals. This example implementation has a variety of types of status signals which are particularly suited for contact tracing applications. In some implementations, the information and/or associations can be provided to one or more electronic communication devices, in which the electronic communication device that receives the information and/or associations can construct the networks described herein, such as the contact proximity networks. Other application domains can collect analogous status signals that are relevant for their particular applications.

Unverified Positive Test

In some implementations, a user can use a user interface within a mobile app on their electronic communication device, to record status signals such as an unverified (self-reported, without any proof provided to the system) positive test result. Recorded status signals can include metadata as well, such as date and time of symptom onset, and symptom characteristics. In some implementations, the user interface can be provided on a website or on a mobile app on a different electronic communication device, first authenticating the user's identity.

Verified Positive Test

In some implementations, a status signal, such as a positive test as previously described, can be verified by a trusted user. An example method of verification can involve a central authority supplying the trusted user with a unique one-time use verification code, with the trusted user relaying this code to the ordinary user to verify their positive test result. The ordinary user can enter this code on their mobile app on their electronic communication device (or on another mobile app or on a website after authenticating their identity). A central authority recognizes the first usage of this code as verification (proof of authenticity) of the self-reported positive test. In some implementations, a trusted user directly communicates, using an electronic communication device, with a central authority, supplying identifiers that characterize the users to label as verified positive. Examples of identifiers with respect to the example implementation can include temporary identifiers associated with users, or unique device IDs, or user IDs. Also (or alternatively) a decentralized network of trust can be used in lieu of a central authority, and each verification can optionally be attributed to the trusted user who issued the one-time use verification code which was entered.

Verified Contact of a Positive Test

In some implementations, contact tracers working on behalf of a trusted user (e.g., at a government or university) can identify that certain user(s) have had close-proximity contact with a positive case. Then, just like the case of the Verified Positive Test, a central authority can supply the trusted user with a unique one-time use code, and the trusted user can relay the code to the ordinary user(s), who enter it in a similar manner to above. In some implementations, a trusted user can directly communicate with a central authority, supplying status signals (e.g., identifiers) that characterize the users to label as having been verified contacts of a positive case. The communications between contact tracers, the central authority and trusted users can be achieved using electronic communications as described herein. Also (or alternatively) a decentralized network of trust can be used in lieu of a central authority, and each verification can optionally be attributed to the trusted user who issued the one-time use verification code which was entered. Also, some implementations may permit a user to report a status signal that they are an unverified contact of a positive test (whereby they declare to have been in close physical proximity to a positive case, without supplying proof of authenticity).

Positive Test Corresponding to Location

In some implementations, unilateral interaction collections can also include scanning location-specific QR codes or touching near-field communication (NFC)-enabled devices. Unilateral interaction collections can include latitude/longitude/elevation measurements, with times recorded. Similar mechanisms (unverified or verified) as described previously can be used to record corresponding status signals (e.g., positive tests that occurred at a location). Referencing the Interaction Collection Subsystem, appropriate status signals can then be assigned to the relevant users.

In some implementations, a user can use a user interface as previously described to self-report symptoms. This can be done before or after a positive test result, for example.

Additional Sensor Data

In some implementations, onboard or external sensors can be used to collect relevant data. For example, a microphone in a mobile device can be used to analyze the audio characteristics of a cough, or a sensor can be used to estimate a user's temperature. Additional sensor data can include symptom information. Users can be allowed to voluntarily enter various symptom information (e.g., fever and loss of sense of smell) or vaccination information (e.g., a date and type of vaccination).

In some implementations, there are different levels of trusted users, and in some implementations, the identity of the trusted user who confirmed a status signal may be made public to some or all other users.

In some implementations, trust is defined by a network of trusted users. Trusted users can then indicate that other users are worthy of trust, forming a directed network, for example where an edge from Trusted User A to Trusted User B indicates that A trusts B. This network of trust can then be leveraged using standard techniques to provide increasing levels of verification to status signals submitted through this subsystem, even in situations where there is no central authority.

Notification Calculation and Delivery Subsystem

In general, a Notification Calculation and Delivery Subsystem can be used to generate and deliver a variety of types of messages about status signals appearing in a network, communicating their approach in the context of the network. The Notification Calculation and Delivery Subsystem can provide particular applications associated with contact tracing, but the subject matter of the present disclosure has broader applications. Leveraging other subsystems in this disclosure, this present disclosure introduces a shift in the type of intervention that can be deployed in application spaces such as contact tracing: early warning of status signals approaching a user over time, based on the structure of the network (as opposed to only geographical proximity).

Some conventional "post-exposure" techniques may first identify positive cases, and then explore a corresponding physical interaction network by asking users in the network to recall contacts that they spent substantial time in close proximity with. Those contacts are then asked to recall their contacts, and so on. There has been significant work on digital approaches to accelerate and automate this process, necessitated by the speed of pre-symptomatic spread of COVID-19. In the traditional model, people or businesses contacted in this method are often asked to self-quarantine and isolate or close because they are suspected to already be infected. This creates an unfavorable user experience since when the contact tracing procedure interacts with a user, the user is asked to engage in behavior which negatively impacts them individually, although positively impacting the community as a whole. This creates issues for adoption and compliance.

By using the subsystems in this disclosure, it is possible to preemptively collect information about the close-proximity interaction network (using centralized or decentralized architectures), and to use that information to calculate and rapidly deliver "pre-exposure" notifications of status signals. In the example context of controlling a contagion, this includes informing users who are much farther away from the status signals (in terms of network-distance on the interaction network) than could be reached with traditional contact tracing. This unlocks the possibility of delivering a favorable user experience in which a user is notified of an incoming wave of infection before they themselves are infected, with useful information that can help them protect themselves from being infected in the first place.

Techniques of the present disclosure can be used to overcome disadvantages of conventional systems, such as systems that record status signals only identifying positive cases. Such conventional systems have several shortcomings: (1) people who are positive may already be in a bad state of mind and may not enter their status; (2) people may be reluctant to tell others that they were actually positive; and (3) there may be negative correlation between people who are positive and people with the app installed.

Note that in the techniques of the present disclosure, status signals identifying contacts of positive cases are already almost as useful as status signals identifying positive cases themselves. This is because if a user learns that at network-distance D from them, there is a contact of a positive case, then the user knows that there is a positive case at network-distance less than or equal to D+1 from them. The techniques therefore achieve an enormous gain compared to the conventional techniques, because use of the techniques provides the benefit from the entry of not only positive cases, but contacts of positive cases. For example, if a positive case has 10 contacts as determined through a manual contact tracing process, each of which is supplied a verification code to report their status as a verified contact of a positive case, the system then has 11 chances to receive useful status signals, whereas a traditional system relying on positive case reports alone only has 1 chance from the positive case itself. This type of status signal naturally generalizes to a type of report that a person is within network-distance C of a positive case. If a user learns that there is a person at network-distance D from them, who has reported that they are within network-distance C of a positive case, then the user knows that there is a positive case at network-distance less than or equal to D+C from them.

Using the network-distance framework, information is collected and reports are produced indicating to the user, for example, that some person at network-distance D from them was a direct contact of a positive case. This implies that a positive case is at network-distance less than or equal to D+1 from the user. A network-distance of 2, for example, means that a first person physically spent time around a second person who physically spent time around a third person (who did not physically spend time around the first person, according to the information known to the system). A status signal can be accepted of a first person being a direct contact of some positive case, and a notification can be provided to everyone in terms of their network-distance to that first person.

Status signals can also be received indicating that a person was C (e.g., C=1 or more) physical relationships away from a positive case, in the sense that there is a sequence of C close-proximity physical interactions connecting from them to the positive case, passing through C−1 distinct intermediate people (who may or may not be app users). If a user finds out that a person at network-distance D away from the user is C physical relationships from a positive case, then the user knows for sure that there is a positive case within less than or equal to D+C physical relationships from the user. Notifications can be provided to all other users identifying their network-distance to the status signals, such as using the user interfaces presented in FIGS. 1D, 1E, 2A and 2B.

This also effectively creates a dynamic in which, as the infection approaches a region of the physical relationship network, app users in that region take greater caution out of self-protection instinct. That increased caution causes the infection to spread more slowly, possibly even below the threshold for exponential growth of infection. Indeed, this technique enables a new approach to infection control: instead of only quarantining after exposure, a population dynamically modulates its behavior so that life can remain relatively normal except in pockets of infection, where people automatically distance (out of selfish desire for self-preservation) and prevent further spread.

This approach also solves adoption issues, because people who wish to protect themselves from the spread of an infection can choose to install an app which directly protects them from infection. Due to the interconnectedness of human relationships, the app itself is useful even at low installation rates (as long as the network of app users remains connected to propagate information). If a subset of the population installs the app, then even if others do not install it, that subset will receive early warning that is sufficiently useful for users to take cover in time to protect themselves. In contrast, the post-exposure technique mainly allows app users to voluntarily sacrifice to protect others. Subsequent sections of this disclosure discuss example implementations of pre-exposure and post-exposure notifications.

Pre-Exposure Warnings

The Interaction Collection Subsystem has the capability to construct a variety of networks. The Status Signal Collection Subsystem supplies status signals. These status signals can be relayed to users in terms of network-theoretic distance in a particularly useful way as follows. The Interaction Collection Subsystem constructs a network based on the close-physical-proximity interactions that occurred during a certain time window (for example, the past two weeks). In some implementations, each user is a distinct node in that network. The status signals from the Status Signal Collection Subsystem are overlaid on the nodes of the network. All of the above can be done in a centralized or decentralized manner.

Status signal information is communicated to users in a format which includes information based on the network-theoretic distance between the node associated with the status signal and the node corresponding to the user. For example, this could appear as a bar chart that indicates the number of status signals recently reported by other users at each network-theoretic distance from the user, or as a text notification, or an animation, or a text display, etc. Information can also be displayed about status signals that are connected to the user at all (within finite network-theoretic distance). In some implementations, estimates may be communicated instead of exact counts (e.g., to improve computational efficiency). In some implementations, these communications arrive in an app on some or all of a user's device(s). In some implementations, these communications are delivered to the user via other means (e.g., mobile text message, phone call, email message, or via a web portal).

It can be particularly useful to display a user interface which allows the comparison of how the above information has changed over time (e.g., by collecting and re-computing displays of status signal information for different parameter sets that correspond to different time windows). This can be done, for example, through an animation, or with direct user-interactive control of the time parameter, for example, to display information for a sequence of time steps. This communicates the approach of the status signals being reported by users with respect to the physical relationship network, analogously to how an animated weather radar map communicates the approach of a storm with respect to geography. In some implementations, a prediction can be made for which users are likely to report status signals in the future (e.g., positivity for a contagion), and is also communicated using an analogous user interface.

Figure 1D:
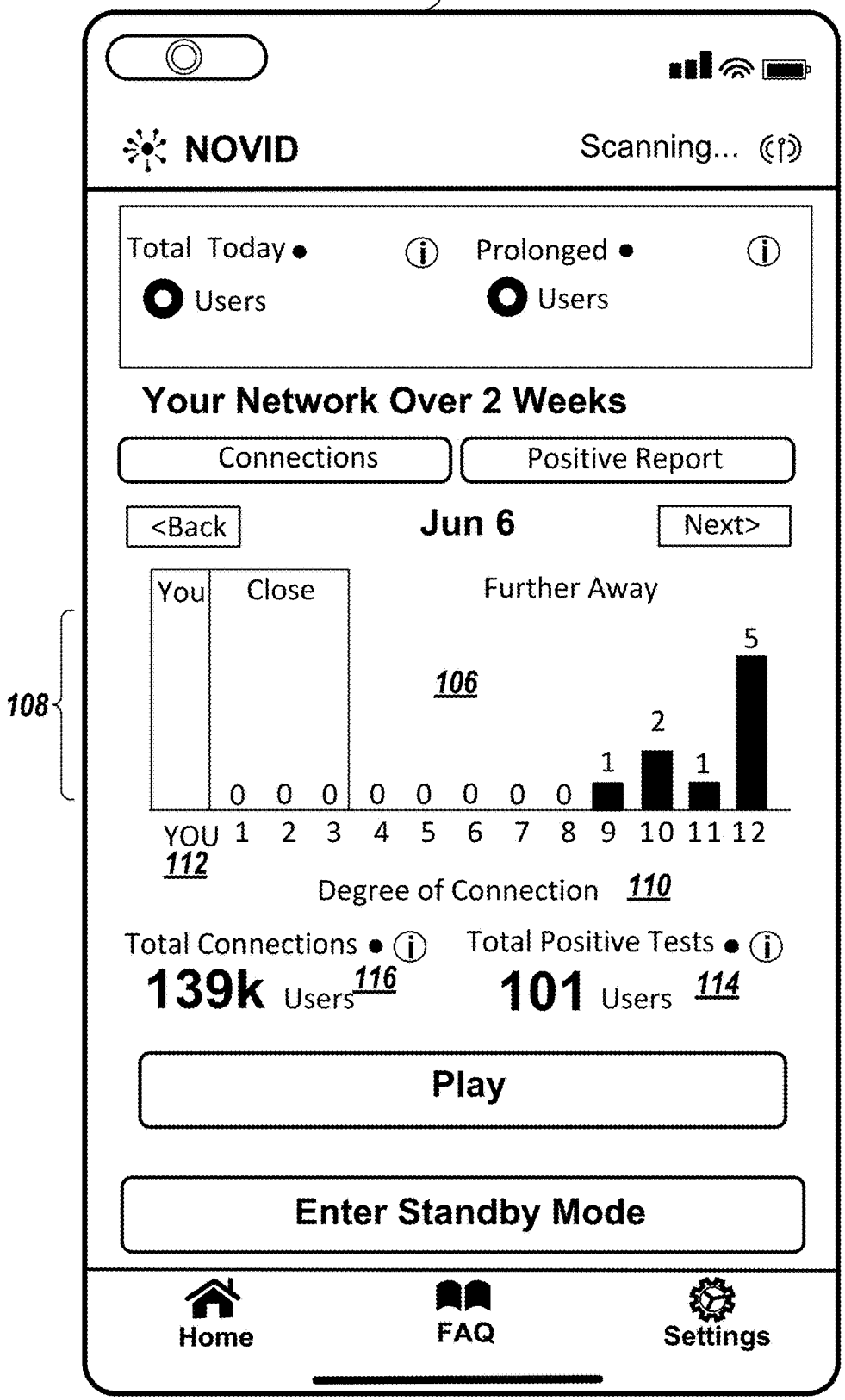
FIGS. 1D and 1E are screenshots collectively showing example displays of a pre-exposure warning system, according to some implementations of the present disclosure.
Figure 1E:
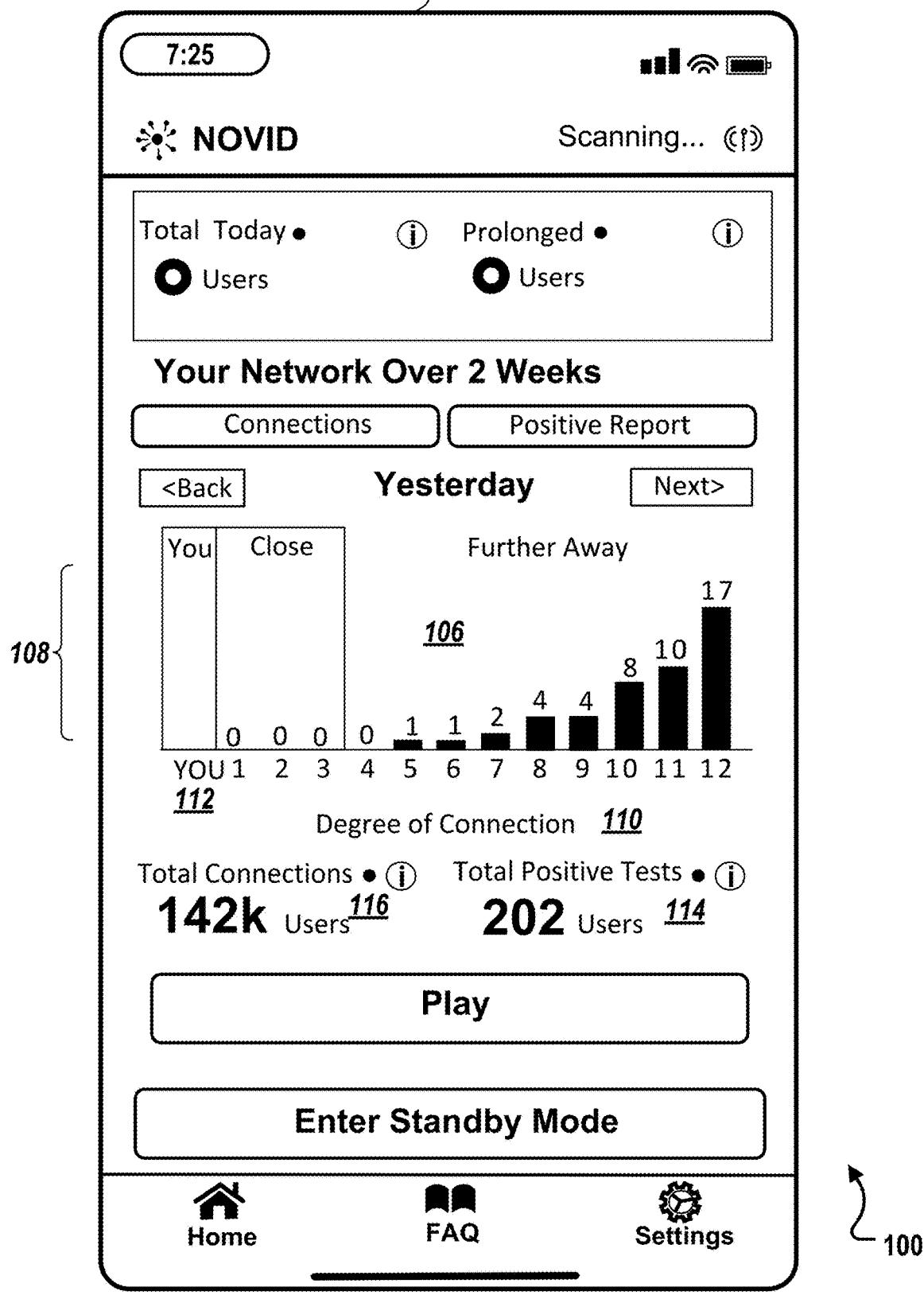

FIGS. 1D and 1E are screenshots collectively showing example displays of a pre-exposure warning system 100, according to some implementations of the present disclosure. Images 102 and 104 indicate two frames of an animated display, indicating the approach of a contagion. Some implementations may filter the status signals by type or verification status. The pre-exposure warning system 100 can be implemented as an application (app) executing on a user's mobile device, such as a cell phone, wearable computing device, or laptop computer. FIGS. 1D and 1E ae just examples of how status signal information can be presented to a user. Other methods for communicating this information can include, for example, a text notification that says "a new infection struck 3 relationships away from you."

The overarching theme of this part of the interface is that it interprets information in terms of network-theoretic distance or connectivity with respect to the interaction network, and communicates that in a digestible way. The information to be relayed can be calculated from any subset of the status signals received, and can even be information simply about the network itself (e.g., how many nodes are at each distance). This section describes one example implementation based on bar charts, but a wide variety of other implementations are possible (e.g., based on text notifications only).

By displaying the evolution of this information over time (for example in a bar chart 106 of positive tests 108 vs. network-distance 110, indicating a degree of connection). The network-distance 110 visually indicates, to the user displaying the information, a relative distance from the user, for example, to other people who are some number of physical connections away from the user (and have tested positive for an antigen, for example). The network-distance is labeled "degree of connection" in the example displays in FIGS. 1D and 1E, but could be labeled with other alternative names such as "degree of separation" or otherwise. A network-distance of 1, for example, indicates a direct physical contact of the user (based on information known to the Interaction Collection Subsystem). A network-distance of 2, for example, indicates a direct physical contact of a direct physical contact of the user (based on information known to the Interaction Collection Subsystem). The bar chart 106 provides a clear indication of objective (e.g., to avoid letting the wave of bars in the chart reach distance 0, which would mean that "you" 112 (a user of the device/app) have tested positive), the information display then takes on a scale-independent nature. Heights of the bar chart 106 indicate a number of users at that distance. Indeed, a user can gauge the speed of approach of the total positive tests 114 towards network-distance 0, and estimate how urgently they need to modulate their social distancing and other precautionary behavior relative to a total number of connections 116. This also makes the system effective even at low installation rates, because as long as the network is connected with some level of connectivity robustness, an infection cluster will be seen coming from some distance away. Crucially, this is because the infection spreads on a very similar network to what is being collected by the Interaction Collection Subsystem. The wave of positive reports may just approach network-distance 0 more rapidly, because of transmission via individuals who are outside of the system. Fortunately, by displaying the evolution of this information over time, a user is still able to estimate how urgently to take precautionary measures.

A display of a sequence of several bar charts like 106 over time can provide or support a visual prediction for future propagation of users reporting the status signals (e.g., if they correspond to a contagion). In some implementations, the system can determine a number of hours or days before a predicted infection of a user based on how fast the status signals are approaching relative to a network-distance from the user to a positive test 114, for example. This is a way, for example, to derive a predicted spread of a specified status signal (e.g., positivity) along at least part of the contact proximity network of a user. The network-distance can be defined as a number of edges connecting, including through any intermediate nodes, a network node representing the user to another network node representing another person who has tested positive for an antigen, for example. The specified status signal can include, e.g., positivity for a contagion. Alternatively, or in addition, the specified status signal can include a non-transmissible feature, such as data indicating that an individual has been vaccinated, data indicating that an individual has purchased a product, data indicating that an individual has interacted with digital content (e.g., viewed an online video or clicked on a link), data indicating that an individual has a reached a specified threshold or goal in a particular activity, among other types of non-transmissible features.

Figure 2A:
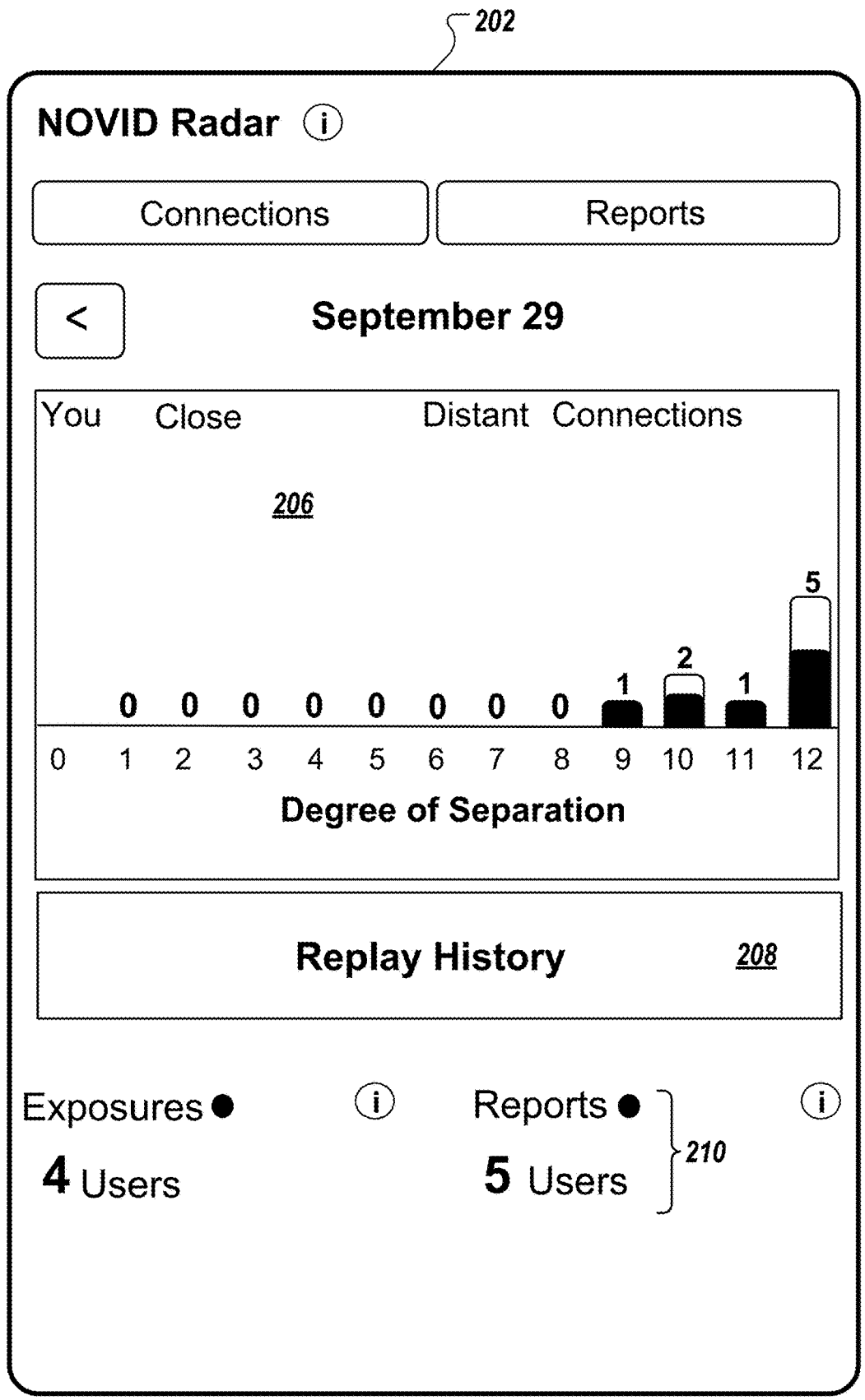
FIGS. 2A and 2B are screenshots collectively showing example displays of a pre-exposure warning system, with both positive cases and contacts of positive cases, according to some implementations of the present disclosure.
Figure 2B:
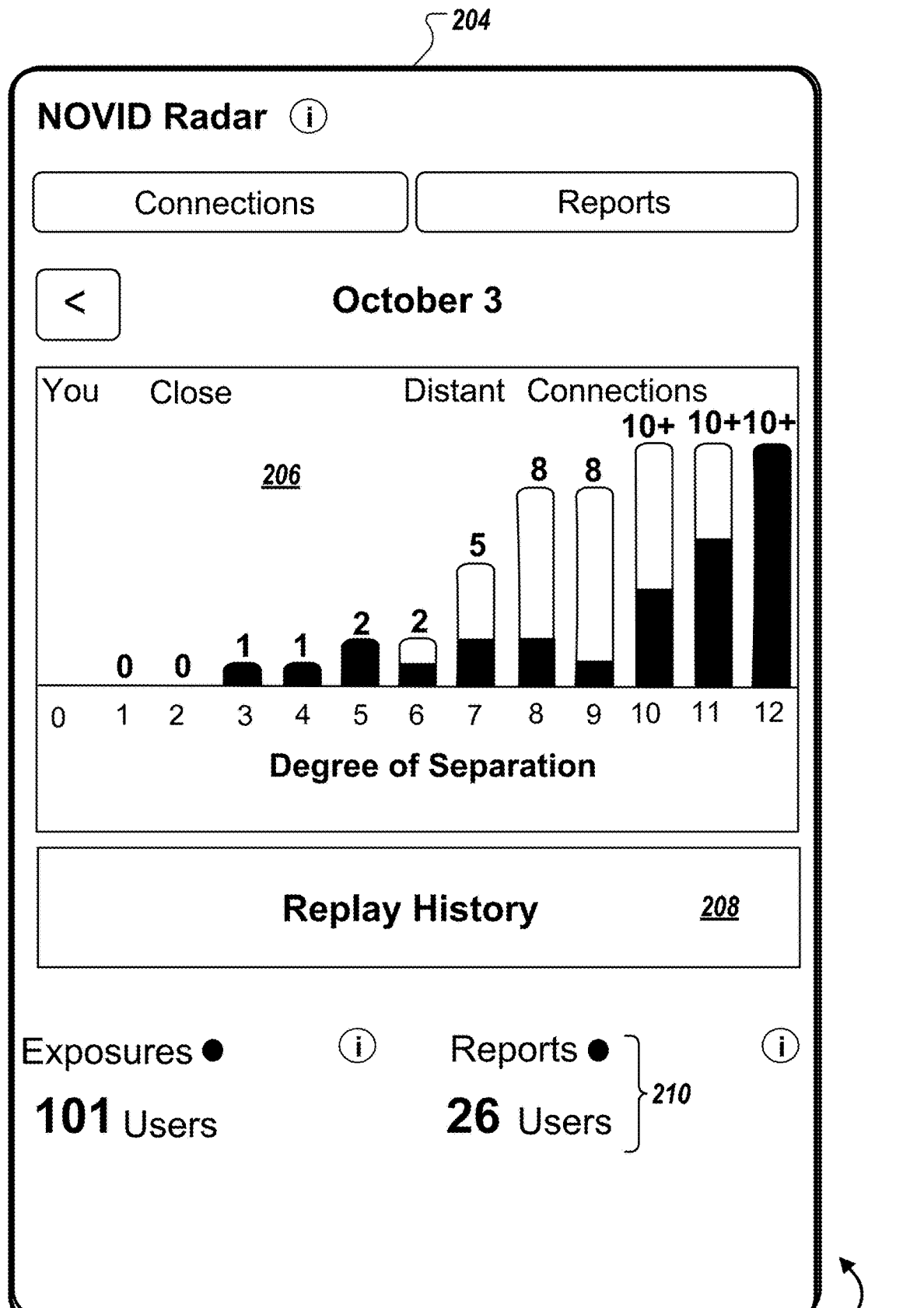

FIGS. 2A and 2B are screenshots collectively showing example displays of a pre-exposure warning system 200, with both positive cases and contacts of positive cases, according to some implementations of the present disclosure. In images 202 and 204, the darker parts of each bar of graphs 206 indicate how many positive cases are at each network-distance, and the lighter parts of each bar of the graphs 206 indicate how many contacts of positive cases are at each network-distance. The pre-exposure warning system 200 can be implemented as an application (app) executing on some or all of the user's mobile device(s), such as a cell phone, wearable computing device, or laptop computer. An example implementation of the pre-exposure warning system 200 includes the following. A replay history control 208 allows the user to cycle through a sequence of graphs 206 over time. Exposures/reports statistics 210 provide a count of users within a particular network-distance of the user who have been exposed and users who have reported being positive (e.g., for the pathogen).

A program performs computation for this notification system on a periodic basis. This can be done in a centralized or decentralized fashion. When the program awakes (e.g., on centralized server(s) or in a possibly asynchronous decentralized framework with each computational device operating on a subset of the full data), it calculates some number of (e.g., 7) frames of data for display on user interfaces. Each frame corresponds to a date-and-time T, and the (e.g.) 7 frames correspond to values of T that are spaced, for example, exactly 24 hours apart, with the most recent value of T corresponding to a time within the last 24 hours of the present. The frame corresponding to T is calculated as follows (with numeric values of time and distance being only non-limiting examples).

The Interaction Collection Subsystem constructs a network (in a centralized or decentralized way), where each node corresponds to a user, and two nodes have an edge between them precisely when, during the time window including, for example, the 336 hours (14 days) leading up to T, there was a total of at least 15 minutes, for example, during which the users had devices within 10 meters, for example, of each other or within audio transmission range. (More complex criteria are possible, as described in the section of this disclosure on the Interaction Collection Subsystem, thanks to the richness of information collected.)

The Status Signal Collection Subsystem identifies reported positive tests which have metadata corresponding to symptom onset between 7 days before T, and 2 days after T (representing a situation where infectiousness begins 2 days before symptom onset and lasts until 7 days after symptom onset, but where different particular numerical values can be used, and they can be independently switched between before/after T based on the application; for example, another implementation might have infectiousness begin 1 day after symptom onset and last until 6 days after symptom onset, in which case the metadata would correspond to symptom onset between 6 days before T, and 1 day before T). In this example implementation, we refer to these as "recently positive nodes". Those corresponding nodes are labeled as "to-be-counted" for the purpose of this example implementation. Analogous procedures can be carried out for other status signals, whereby some subset of the nodes is labeled "to-be-counted" using criteria which may include status signal information and various times associated with that status signal information. In some implementations, it is also desirable to report to each user how many other users are at various network-distances, at which point the analogous procedure could be carried out where every node is labeled "to-be-counted".

For each node, an estimate is made for how many to-be-counted nodes are at each network-theoretic distance from 0 to 12 (this number can be changed for different implementations, and the resulting algorithms adapt accordingly). This step is nontrivial because the number of nodes can be very large (in the billions). This procedure may also be repeated for several different to-be-counted subsets (e.g., corresponding to users reporting positive tests, or status as being a contact-traced contact of a positive case, or symptoms, or vaccination status, or more generally for any status signal type collected by the Status Signal Collection Subsystem, or simply with the to-be-counted subset being the entire set of nodes). A sample implementation of a time-and-space computationally efficient algorithm is provided. In some implementations, when data is needed for display on an app interface on a device, the device requests its data for the last (e.g.) 7 frames. In implementations which perform network computations out to some bounded distance (e.g., 12) from each user, decentralized architectures are feasible because the computed information for each user does not require full knowledge of the entire network.

In the current example, the user's app creates and displays several sets of (e.g.) 7 or more bar charts. One set of bar charts corresponds to recently positive nodes, and one set of bar charts corresponds to total nodes at various network-distances. One set of bar charts corresponds to recently reported contacts of positive cases. Each bar chart has a horizontal axis corresponding to the network-distance from the user, and a vertical axis corresponding to the estimated number of recently positive nodes (or total nodes, or number of recently reported contacts of positive cases) at that network-distance.

The app also displays summary statistics estimating how many total nodes or recently positive nodes are connected to the user in the network via a path of any length. The app user interface allows the user to easily visualize how the frames evolve over time, through an animation feature. In some implementations, it is desirable that if one recently positive node contributes +1 to (adding one to the height of) the bar at network-distance D in one animation frame (corresponding to a 24-hour time window), then if that same recently positive node contributes to the next animation frame, it contributes +1 to the bar at network-distance D again. The above example implementation does not have this property, because it is possible for the network to have changed by the next frame, affecting the network-distance. A simple example resolution is to, for each 24-hour window, compute the network as above based on interactions during the 336 hours ending at the end of the 24-hour window, but using the Status Signal Collection Subsystem to identify nodes that reported positivity with symptoms starting between 1 and 2 days after T (say). Now, for each 24-hour window, there is a vector including the numbers of recently positive nodes at each network-distance. When the app displays this information to the user, it can display for a given animation frame ending at T (say) the pointwise sum of the vectors corresponding to the last (e.g.) nine (2 pre-symptomatic days +7 post-symptomatic days) disjoint 24-hour windows ending at T. Other numerical values can be used in other implementations, possibly with different justifications.

An example implementation of a time-and-space efficient algorithm for estimating the number of to-be-counted nodes at various network-distances from every node follows. The to-be-counted nodes can be identified in the network 176, for example. A hash function H is fixed which sends nodes to numbers in $\{0, 1, 2, \ldots, 1023\}$ (other implementations may use different-sized ranges than 1024, and the resulting algorithms adapt accordingly). A function F(M) is defined to be the maximum likelihood estimator of the number N such that if N independent uniformly random numbers are drawn from $\{0, 1, 2, \ldots, 1023\}$ with replacement, then there are exactly M distinct numbers among them. A 2-dimensional array neighborhood[V][D] is allocated to keep track of to-be-counted nodes at network-distance$\leq$D from node V. Each element of neighborhood[V][D] is a 1024-bit bitstring (representable as an array of 16 64-bit integers to accelerate performance in some implementations).

One pass is made through all vertices. For each node V that is to-be-counted, neighborhood[V][0] is set to be the 1024-bit bitstring which is 0 everywhere except 1 at the index H(V).

Twelve passes are made, letting D run from 1 to 12. In the D-th pass, for each node V, let neighborhood[V][D] be the bitwise-OR of all 1024-bit bitstrings corresponding to neighborhood[U][D−1] for every node U which is adjacent to V or equal to V itself. The estimated number of to-be-counted nodes at network-distance$\leq$D from V is F(M), where M is the number of 1's in the bitstring neighborhood[V][D]. If the number M above is less than some threshold (e.g., 800), then the number of to-be-counted nodes at network-distance exactly D from V can be estimated to be the difference between the number at network-distance<D and at network-distance$\leq$D−1. Note that since in this implementation, the neighborhood[anything][D] values are updated using the neighborhood[anything][D−1] values, without using neighborhood[anything][<D−1] values, more efficient implementations are possible, such as by having the second array index only be 0 and 1 (the parity of D). However, this disclosure is written in terms of the above procedure to simplify ease of understanding.

The algorithm completes in time linear in the number of edges in the network. It has the property that if there are any to-be-counted nodes at network-distance$\leq$D from a node V, then the estimated number of to-be-counted nodes at network-distance$\leq$D from a node V is definitely at least 1. Due to the use of hashing, there is a chance that the function F is imprecise at estimating the true number of to-be-counted nodes due to the randomness of hash collisions. However, this will be sufficiently useful for contact tracing purposes. Indeed, it will provide reasonably accurate counts of to-be-counted nodes until the numbers of to-be-counted nodes within given network-distance reach beyond about 1000 nodes.

In some implementations, it is useful to provide reasonably accurate counts even at network-distances beyond when the numbers of to-be-counted nodes exceed 1000. Some implementations may report estimates of the numbers of nodes (not just recently positive nodes) at various network-distances from the user, which may easily exceed 1000. For that, a probabilistic approach enables the estimation to still operate with both time and space efficiency.

An example implementation of a time-and-space efficient algorithm for estimating the number of to-be-counted nodes at various network-distances from every node can include the following. Each to-be-counted node is randomly marked as "flagged" independently with some probability P. The same algorithm is performed, counting flagged nodes instead of to-be-counted nodes. Whenever the algorithm gets values 100<M<800, for example, F(M) (which now estimates the number of flagged nodes within a given network-distance) can be divided by P to deduce an estimate of how many to-be-counted nodes (not only flagged nodes) are at network-distance less than or equal to D from V.

The procedure can be repeated several times with the same or different P, with the results averaged, to produce more accurate estimates. The procedure can be performed with exponentially decreasing values of P (e.g., 1/30, 1/900, 1/2700, 1/81000, etc.) so that the different values of P provide reliable estimates at different scales of the network-distance-exactly-D count of to-be-counted nodes from the perspective of each node. Note that as stated, this example algorithm computes all of its counts for a given user based on information from users within some fixed network-distance of that given user. Consequently, it naturally generalizes to decentralized computational infrastructures, because it only uses a part of the full network in order to compute the outputs for each individual user. For example, a simple way of decentralizing the computational framework would be to have each individual device maintain a model of the network within distance 12 of its user (updated based upon user-to-user interactions shared between directly connected nodes in a decentralized manner), and to perform its own computations.

Post-Exposure Warnings

This system can also be used to rapidly send post-exposure notifications. In the context of assisting traditional contact tracing, this would significantly accelerate the rate of identifying potential contacts. In some applications, if User A is associated with a new positive test result, it is useful to identify not only any User B that had extended close-physical-proximity contact with User A during a certain contagious period (e.g., 9 days), but also any User C that had extended close-physical-proximity contact to User B at least (e.g.) 4 days (an incubation period) but at most (e.g.) 13 days after the contact between Users A and B. In some applications, it may even be useful to calculate further iterations.

Such warnings are efficient for the framework in this disclosure to estimate and send. Indeed, all calculations can be batched and computed in parallel in a background server-side task, as follows. This procedure can also be decentralized in a natural way because each user's received signals are computed using information from other users within a given network-distance. The Status Signal Collection Subsystem identifies contagious periods for all newly reported status signals in this batch, and associates this data with users (nodes). In some implementations, recently reported status signals are included as well even if they are not newly reported. For the time period of interest, time is partitioned into disjoint 12-hour time intervals (different values can be used in different implementations, and the subsequent steps adapt accordingly). The Interaction Collection Subsystem constructs a network for each 12-hour time interval. For each node, this algorithm maintains a record of its earliest time interval of being reached by a contact chain from a positive report, and if reached, the length of that contact chain. Initially, all nodes have no time of being reached by a contact chain. The algorithm iterates from one time interval to the next, performing a number of iterations equal to the number of time intervals. In each iteration, if a node newly became contagious during this time interval, its record is updated to have a contact chain of length 0, reached by a contact chain at this time interval. In the network corresponding to this time interval, if any node V has a direct neighbor U in this network whose time reached by a contact chain is at least (e.g.) 4 days before this time interval, and whose contact chain length plus 1 is strictly less than the contact chain length at V (or U has been reached by a contact chain but V has not), the record of V is updated to have a contact chain length equal to U's contact chain length plus 1, reached at this time interval. Nodes are then notified which have been reached by a contact chain of the length of their contact chain. In some implementations, these warnings are then sent from a central authority to the relevant devices as notifications, or retrieved by the devices in order to update their user interfaces, or computed on the devices themselves via a decentralized framework.

Pre-Exposure Warnings

FIG. 3 is a flowchart of an example of a method 300 for providing a pre-exposure warning system, according to some implementations of the present disclosure. Providing a pre-exposure warning system provides a benefit over conventional systems that are reactive in nature, providing solely post-exposure information. For clarity of presentation, the description that follows generally describes method 300 in the context of the other figures in this description, including FIGS. 1A-2B. However, it will be understood that method 300 can be performed, for example, by any suitable system, environment, software, and hardware, or a combination of systems, environments, software, and hardware, as appropriate. In some implementations, various steps of method 300 can be run in parallel, in combination, in loops, or in any order. In some implementations, method 300 can produce something other than, or in addition to, a graphical display. For example, non-graphical techniques can be used to display how information changes over time, such as by displaying only text, or showing a whole family of different charts (e.g., one per day) for communicating information about the contagion, where one of the attributes of the information is network-distance. Information that is presented can support the concept of using the network-distance with other information, such as dates and numbers of cases. The spread of a contagion can be tracked in terms of the network-distance, and information that references the distance can be communicated to the user.

At 302, information about a first electronic communication device is transmitted from the first electronic communication device to at least one server, and/or to a decentralized infrastructure. The information about the first electronic communication device includes vicinity information about a vicinity of the first electronic communication device. In general, "vicinity information" can include information, collected from the first electronic communication device and/or from its communication with nearby or remote electronic communication devices (which may or may not be directly participating in the system), which can be directly used, or indirectly combined with information collected from other electronic communication devices, to estimate relative physical space and time proximity between multiple users participating in the system. For example, information about a second electronic communication device that is within a vicinity of a first electronic communication device can be generated, stored, and transmitted by the first electronic communication device. For example, the at least one server or decentralized infrastructure can 1) modify a contact proximity network based, in part, on the information about the second electronic communication device; and 2) inform users about status signals reported by other users, in the context of network-distance. As an example, a duration can be determined over which the first electronic communication device is within a predefined vicinity of the second electronic communication device. The first electronic communication device and/or the second electronic communication device optionally are mobile electronic communication devices. As an example, the information can include one or both of: 1) a physical distance of the second electronic communication device from the first electronic communication device, and 2) an indicator of an audio, radio-frequency (e.g., BLUETOOTH, ULTRA-WIDEBAND, etc.), optical, or infrared signal emitted by the second electronic communication device and/or an indicator of an audio, radio-frequency, optical, or infrared signal emitted by the first electronic communication device. Identifying information about the second electronic communication device can include bilaterally communicating with the second electronic communication device to obtain (possibly temporary) unique identifier information of the second electronic communication device. From 302, method 300 proceeds to 304.

In some implementations, a system implementing method 300 can include a unilateral interaction collection system, for example one by which a device reports which WLAN access point to which it was attached. The information received in method 300 can be received by one or more of a centralized server and a decentralized cluster (for example, using blockchain technology).

At 304, a status signal associated with a first user of the first electronic communication device (which may or may not be the same as the first electronic device in 302) is transmitted from the first electronic communication device to the at least one server and/or decentralized infrastructure. The Status Signal Collection Subsystem can collect status signals that are relevant to the application context, including symptom information and positive diagnoses and vaccinations, for example. From 304, method 300 proceeds to 306.

In some implementations, an indicator can be received from a third device reporting a status signal on behalf of at least one user.

In some implementations, a trusted authentication rating can be assigned to the indicator received from the third device. In some implementations, an exposure notification can be output that is indicative of a contact proximity to a potential source of exposure to a transmissible feature, where the contact proximity to the potential source includes a geographical distance to the potential source of exposure to the transmissible feature and/or a network-distance along the contact proximity network to the potential source of exposure to a transmissible feature.

In some implementations, method 300 can further include dynamically updating a status signal proximity graphic to indicate a contact proximity network-distance to a status signal, and outputting the status signal proximity graphic, where optionally the status signal proximity graphic includes a chart.

In some implementations, method 300 can further include receiving, as an input to the first electronic communication device, an indicator that a user of the first electronic device is reporting a status signal, for example, if the user self-reports as having tested positive for a virus.

At 306, contact proximity network information about a contact proximity network is received from the at least one server and/or decentralized infrastructure, and is stored. The contact proximity network is based, in part, on the information about the first electronic communication device and information about the second electronic communication device in 302. The contact proximity network information includes status signal information associated with users within the contact proximity network. The contact proximity network includes a plurality of interconnected nodes, where each node of the plurality of interconnected nodes corresponds to a different user. For example, a contact proximity network is updated in a centralized or decentralized way using information about the second electronic communication device and information about the first electronic communication device, or unilaterally collected information from the first device. Identifying information about the second electronic communication device can include determining a physical distance between the first electronic communication device and the second electronic communication device based on an audio signal, a radio-frequency signal (e.g., BLUETOOTH, ULTRA-WIDEBAND, etc.), an infrared signal, and/or an optical signal emitted by the first electronic communication device and/or by the second electronic communication device. Determining the distance between the first electronic communication device and the second electronic communication device can optionally be based in part on an audio signal, for example.

In some implementations, generation of all or a part of the proximity network can occur on a centralized server and/or a decentralized infrastructure. In these and other implementations, mobile devices can submit contact information and receive, from the server and/or decentralized infrastructure, displayable output which includes information based on the proximity network. Interactions between devices and the server and/or decentralized infrastructure can occur in real-time, such as within minutes (e.g., five) or seconds (e.g., 30) of sending contact information and updating the network. In some implementations, user-configurable settings can be set by the user to control the timing of updates from the server.

In some implementations, the contact proximity network represents pairwise interactions between the users of the first and second electronic communication devices. The contact proximity network includes proximity information amongst a plurality of users, where the proximity information may include a geographical distance, a network distance along the contact proximity network, and/or a frequency of contact between users. The proximity information may include: 1) current vicinity information related to a current geographical distance between users, a current network distance between users, and/or a current geographical distance between mobile electronic communication devices associated with users; 2) past vicinity information related to a geographical distance between users, a network distance between users, and/or a geographical distance between mobile electronic communication devices associated with users during a past period of time; 3) time information related to when users and/or associated mobile electronic communication devices were within a defined vicinity relative to one another; 4) and/or duration information related to how long users and/or associated mobile electronic communication devices where within the defined vicinity relative to one another. In some implementations, a predicted spread of users reporting the specified status signal (e.g., a transmissible feature such as positivity for a contagion) along at least part of the contact proximity network can be derived, such as by evaluating historical spread of the specified feature over time. From 306, method 300 proceeds to 308.

At 308, a user notification indicating a network-based proximity of a first user in the contact proximity network to a second user in the contact proximity network is provided using the contact proximity network information received from the at least one server. The second user is identified as associated with a specified status signal within a specified time frame. The network-based proximity of the first user to the second user is a minimum number of connections between the first user and the second user along the contact proximity network during the specified time frame. For example, a graphical display including a dynamically updatable chart illustrating a network-distance, in the contact proximity network, of a first user to at least one relevant status signal may be provided. The Status Signal Collection Subsystem can collect status signals that are relevant to the application context, including symptom information and positive diagnoses and vaccinations, for example. As an example, the dynamically updatable chart can illustrate a time-evolution of the network-distance of the first user to at least one relevant status signal, such as described with reference to FIGS. 1A-2B. The graphical display uses information received from the at least one server or decentralized infrastructure. As an example, a time-evolution graphic can be output that depicts a spread of positive cases along at least part of the contact proximity network, where the time-evolution graphic optionally includes a representation of number of positive cases as a function of network-distance along the contact proximity network. In some implementations, a post-exposure notification can be output to alert users or devices exposed to a potential source of exposure to the transmissible feature. While step 308 is associated with a graphical display, non-graphical displays can also be used in this and other displays described within the present disclosure. Step 308 can be used to provide any status signal relevant to a contagion, including an exposure or a positive test or a vaccination, where network-distance from the user is one of the attributes.

In some implementations, a display can include new information about new status signals arriving, and the user can be informed of network-distances between the user and the new status signals. In some implementation, a sequence of graphs can provide an animation over time. In some implementations, the system can send text-based notification messages containing raw information such as "new status signal at network-distance X from you." Techniques of the present disclosure can be used to compute the information in this network-distance framework, and then display the information to the user. In some implementations, instead of a bar chart, icons representing people can be displayed, with a chain of relationships of the length corresponding to how far away (in network-distance) a new status signal is from the user. In some implementations, this information appears on an app on some or all of the user's device(s). In some implementations, this information is sent to the user via other means, such as mobile text messaging, phone calls, email messages, or websites. After 308, method 300 can stop.

Figure 4:
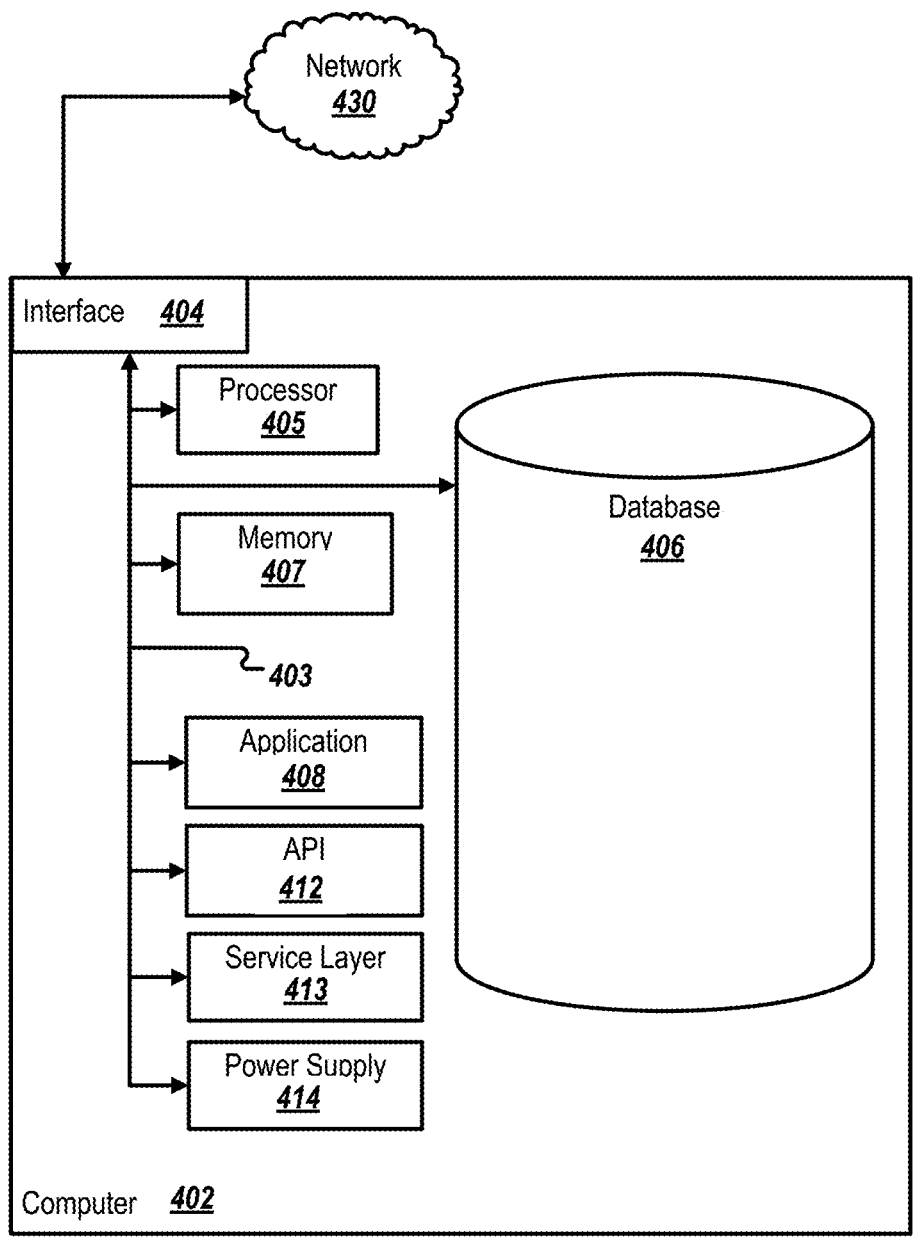
FIG. 4 is a block diagram illustrating an example computer system used to provide computational functionalities associated with described algorithms, methods, functions, processes, flows, and procedures as described in the present disclosure, according to some implementations of the present disclosure.

FIG. 4 is a block diagram of an example computer system 400 used to provide computational functionalities associated with described algorithms, methods, functions, processes, flows, and procedures described in the present disclosure, according to some implementations of the present disclosure. The illustrated computer 402 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 402 can include input devices such as keypads, keyboards, and touch screens that can accept user information. Also, the computer 402 can include output devices that can convey information associated with the operation of the computer 402. The information can include digital data, visual data, audio information, or a combination of information. The information can be presented in a graphical user interface (UI) (or GUI).

The computer 402 can serve in a role as a client, a network component, a server, a database, a persistency, or components of a computer system for performing the subject matter described in the present disclosure. The illustrated computer 402 is communicably coupled with a network 430. In some implementations, one or more components of the computer 402 can be configured to operate within different environments, including cloud-computing-based environments, local environments, global environments, and combinations of environments.

At a top level, the computer 402 is an electronic computing device operable to receive, transmit, process, store, and manage data and information associated with the described subject matter. According to some implementations, the computer 402 can also include, or be communicably coupled with, an application server, an email server, a web server, a caching server, a streaming data server, or a combination of servers.

The computer 402 can receive requests over network 430 from a client application (for example, executing on another computer 402). The computer 402 can respond to the received requests by processing the received requests using software applications. Requests can also be sent to the computer 402 from internal users (for example, from a command console), external (or third) parties, automated applications, entities, individuals, systems, and computers.

Each of the components of the computer 402 can communicate using a system bus 403. In some implementations, any or all of the components of the computer 402, including hardware or software components, can interface with each other or the interface 404 (or a combination of both) over the system bus 403. Interfaces can use an application programming interface (API) 412, a service layer 413, or a combination of the API 412 and service layer 413. The API 412 can include specifications for routines, data structures, and object classes. The API 412 can be either computer-language independent or dependent. The API 412 can refer to a complete interface, a single function, or a set of APIs.

The service layer 413 can provide software services to the computer 402 and other components (whether illustrated or not) that are communicably coupled to the computer 402. The functionality of the computer 402 can be accessible for all service consumers using this service layer. Software services, such as those provided by the service layer 413, can provide reusable, defined functionalities through a defined interface. For example, the interface can be software written in JAVA, C++, or a language providing data in extensible markup language (XML) format. While illustrated as an integrated component of the computer 402, in alternative implementations, the API 412 or the service layer 413 can be stand-alone components in relation to other components of the computer 402 and other components communicably coupled to the computer 402. Moreover, any or all parts of the API 412 or the service layer 413 can be implemented as child or sub-modules of another software module, enterprise application, or hardware module without departing from the scope of the present disclosure.

The computer 402 includes an interface 404. Although illustrated as a single interface 404 in FIG. 4, two or more interfaces 404 can be used according to particular needs, desires, or particular implementations of the computer 402 and the described functionality. The interface 404 can be used by the computer 402 for communicating with other systems that are connected to the network 430 (whether illustrated or not) in a distributed environment. Generally, the interface 404 can include, or be implemented using, logic encoded in software or hardware (or a combination of software and hardware) operable to communicate with the network 430. More specifically, the interface 404 can include software supporting one or more communication protocols associated with communications. As such, the network 430 or the interface's hardware can be operable to communicate physical signals within and outside of the illustrated computer 402.

The computer 402 includes a processor 405. Although illustrated as a single processor 405 in FIG. 4, two or more processors 405 can be used according to particular needs, desires, or particular implementations of the computer 402 and the described functionality. Generally, the processor 405 can execute instructions and can manipulate data to perform the operations of the computer 402, including operations using algorithms, methods, functions, processes, flows, and procedures as described in the present disclosure.

The computer 402 also includes a database 406 that can hold data for the computer 402 and other components connected to the network 430 (whether illustrated or not). For example, database 406 can be an in-memory, conventional, or a database storing data consistent with the present disclosure. In some implementations, database 406 can be a combination of two or more different database types (for example, hybrid in-memory and conventional databases) according to particular needs, desires, or particular implementations of the computer 402 and the described functionality. Although illustrated as a single database 406 in FIG. 4, two or more databases (of the same, different, or combination of types) can be used according to particular needs, desires, or particular implementations of the computer 402 and the described functionality. While database 406 is illustrated as an internal component of the computer 402, in alternative implementations, database 406 can be external to the computer 402.

The computer 402 also includes a memory 407 that can hold data for the computer 402 or a combination of components connected to the network 430 (whether illustrated or not). Memory 407 can store any data consistent with the present disclosure. In some implementations, memory 407 can be a combination of two or more different types of memory (for example, a combination of semiconductor and magnetic storage) according to particular needs, desires, or particular implementations of the computer 402 and the described functionality. Although illustrated as a single memory 407 in FIG. 4, two or more memories 407 (of the same, different, or combination of types) can be used according to particular needs, desires, or particular implementations of the computer 402 and the described functionality. While memory 407 is illustrated as an internal component of the computer 402, in alternative implementations, memory 407 can be external to the computer 402.

The application 408 can be an algorithmic software engine providing functionality according to particular needs, desires, or particular implementations of the computer 402 and the described functionality. For example, application 408 can serve as one or more components, modules, or applications. Further, although illustrated as a single application 408, the application 408 can be implemented as multiple applications 408 on the computer 402. In addition, although illustrated as internal to the computer 402, in alternative implementations, the application 408 can be external to the computer 402.

The computer 402 can also include a power supply 414. The power supply 414 can include a rechargeable or non-rechargeable battery that can be configured to be either user- or non-user-replaceable. In some implementations, the power supply 414 can include power-conversion and management circuits, including recharging, standby, and power management functionalities. In some implementations, the power-supply 414 can include a power plug to allow the computer 402 to be plugged into a wall socket or a power source to, for example, power the computer 402 or recharge a rechargeable battery.

There can be any number of computers 402 associated with, or external to, a computer system containing computer 402, with each computer 402 communicating over network 430. Further, the terms "client," "user," and other appropriate terminology can be used interchangeably, as appropriate, without departing from the scope of the present disclosure. Moreover, the present disclosure contemplates that many users can use one computer 402 and one user can use multiple computers 402.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to a suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatuses, devices, and machines for processing data, including by way of example, a programmable processor, a computer, or multiple processors or computers. The apparatus can also include special purpose logic circuitry including, for example, a central processing unit (CPU), a field-programmable gate array (FPGA), or an application specific-integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, such as LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as standalone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, subprograms, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory.

Graphics processing units (GPUs) can also be used in combination with CPUs. The GPUs can provide specialized processing that occurs in parallel to processing performed by CPUs. The specialized processing can include artificial intelligence (AI) applications and processing, for example. GPUs can be used in GPU clusters or in multi-GPU computing.

A computer can include, or be operatively coupled to, one or more mass storage devices for storing data. In some implementations, a computer can receive data from, and transfer data to, the mass storage devices including, for example, magnetic, magnetooptical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer-readable media (transitory or non-transitory, as appropriate) suitable for storing computer program instructions and data can include all forms of permanent/non-permanent and volatile/non-volatile memory, media, and memory devices. Computer-readable media can include, for example, semiconductor memory devices such as random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer-readable media can also include, for example, magnetic devices such as tape, cartridges, cassettes, and internal/removable disks. Computer-readable media can also include magneto-optical disks and optical memory devices and technologies including, for example, digital video disc (DVD), CD-ROM, DVD+/–R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated into, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that the user uses. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch-screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations. It should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

What is claimed is:

1. A computer-implemented method, comprising:
    transmitting, to one or more of at least one server and a decentralized infrastructure and from a first electronic communication device, information about the first electronic communication device, wherein the information about the first electronic communication device comprises vicinity information about a vicinity of the first electronic communication device;
    transmitting, to the one or more of the at least one server and the decentralized infrastructure and from the first electronic communication device, a status signal associated with a first user of the first electronic communication device;
    receiving and storing contact proximity network information about a contact proximity network from the one or more of the at least one server and the decentralized infrastructure, wherein the contact proximity network is based, in part, on information from a plurality of electronic communication devices and information about an association between users and the plurality of electronic communication devices, wherein the contact proximity network information comprises status signal information associated with the users within the contact proximity network, and wherein the contact proximity network further comprises a plurality of interconnected nodes, wherein each node of the plurality of interconnected nodes corresponds to a different user and each pairwise connection between two users in the contact proximity network is based in part upon the two users' current or past relative physical space and time proximity; and
    based on the contact proximity network information received from the one or more of the at least one server and the decentralized infrastructure, providing a user notification indicating a network-based proximity of the first user in the contact proximity network to a second user in the contact proximity network, wherein the second user is associated with a specified status signal within a specified time frame,
    wherein, for one or more paths of connections between the first user and the second user, the network-based proximity of the first user to the second user corresponds to a path of connection of the one or more paths having a fewest number of connections between the first user and the second user.

2. The computer-implemented method of claim 1, wherein the vicinity information for the first electronic communication device includes information about a second electronic communication device, wherein the information about the second electronic communication device comprises data regarding a proximity or location of the first electronic communication device relative to the second electronic communication device, and wherein the method further comprises transmitting the information about the second electronic communication device to the one or more of the at least one server and the decentralized infrastructure.

3. The computer-implemented method of claim 2, wherein obtaining information about the second electronic communication device comprises estimating a physical distance between the first electronic communication device and the second electronic communication device based on one or more of an audio signal, a radio-frequency signal, an infrared signal, and an optical signal emitted by one or more of the first electronic communication device and by the second electronic communication device; and by signals between the first and second electronic communication devices and other electronic communication device(s) which are used to estimate the physical distance between the first and second electronic communication devices.

4. The computer-implemented method of claim 1, wherein the status signal is a status of being a physical contact of a person who is positive for a contagion, or more generally, being less than or equal to a specified number of physical contacts separated from a person who is positive for a contagion.

5. The computer-implemented method of claim 1, wherein the user notification is one or more of a text, an animation, and a graphical display.

6. The computer-implemented method of claim 5, wherein the contact proximity network illustrates a time-evolution of contact network distance(s) from the first user to other users reporting status signals during time windows of interest.

7. The computer-implemented method of claim 1, wherein the vicinity information includes information about a second electronic communication device that comprises one or more of:

a physical distance of the second electronic communication device from the first electronic communication device; and data about audio, radio-frequency, optical, and infrared signals emitted by one or both of the second electronic communication device and the first electronic communication device.

8. The computer-implemented method of claim 1, wherein the contact proximity network traces a spread through the contact proximity network, of the users reporting the specified status signal.

9. The computer-implemented method of claim 8,
wherein the contact proximity network represents pairwise interactions between the users,
wherein the contact proximity network comprises proximity information amongst a plurality of users associated with the plurality of electronic communication devices, wherein the proximity information comprises a geographical distance, a network distance along the contact proximity network, and frequency of contact between users' associated electronic communication devices,
and wherein the proximity information comprises one or more of:
current geographical distance between users' associated electronic communication devices, and a current network distance between the users;
past geographical distance between users' associated electronic communication devices, and a network distance between the users during a past period of time;
time information related to when users' associated electronic communication devices were within a defined vicinity relative to one another;
and duration information related to how long users' associated electronic communication devices were within the defined vicinity relative to one another.

10. The computer-implemented method of claim 1, further comprising deriving a predicted spread of the users reporting the specified status signal along at least part of the contact proximity network.

11. The computer-implemented method of claim 1, further comprising outputting a time-evolution graphic depicting a spread of the users reporting the specified status signal along at least part of the contact proximity network, wherein the time-evolution graphic comprises a representation of a number of the users reporting the specified status signal within a specified time window as a function of network distance along the contact proximity network.

12. The computer-implemented method of claim 1, further comprising identifying and outputting a post-exposure notification to users exposed to a user reporting the specified status signal within a specified time frame.

13. The computer-implemented method of claim 1, further comprising transmitting, to the one or more of the at least one server and the decentralized infrastructure, information about at least one user, wherein the information includes an indicator to report specified status signal(s) on behalf of and associated with the at least one user.

14. The computer-implemented method of claim 1, further comprising outputting an exposure notification indicative of the first user's contact proximity to a second user reporting the specified status signal, wherein the contact proximity to the second user comprises a geographical distance and a network distance along the contact proximity network between the two users.

15. A computer-implemented system, comprising
one or more electronic processors,
one or more computer memory devices interoperably coupled with the one or more electronic processors and having tangible, non-transitory, machine-readable media storing one or more instructions that, when executed by the one or more electronic processors, perform one or more operations comprising:
transmitting, to one or more of at least one server and a decentralized infrastructure and from a first electronic communication device, information about the first electronic communication device, wherein the information about the first electronic communication device comprises vicinity information about a vicinity of the first electronic communication device;
transmitting, to the one or more of the at least one server and the decentralized infrastructure and from the first electronic communication device, a status signal associated with a first user of the first electronic communication device;
receiving and storing contact proximity network information about a contact proximity network from the one or more of the at least one server and the decentralized infrastructure, wherein the contact proximity network is based, in part, on information from a plurality of electronic communication devices and information about an association between users and the plurality of electronic communication devices, wherein the contact proximity network information comprises status signal information associated with the users within the contact proximity network, wherein the contact proximity network comprises a plurality of interconnected nodes, wherein each node of the plurality of interconnected nodes corresponds to a different user and each pairwise connection between two users in the contact proximity network is based in part upon the two users' current or past relative physical space and time proximity; and
using the contact proximity network information received from the one or more of the at least one server and the decentralized infrastructure, providing a user notification indicating a network-based proximity of a first user in the contact proximity network to a second user in the contact proximity network, wherein the second user is associated with a specified status signal within a specified time frame,
wherein, for one or more paths of connections between the first user and the second user, the network-based proximity of the first user to the second user corresponds to a path of connection of the one or more paths having a fewest number of connections between the first user and the second user.

16. The computer-implemented system of claim 15, wherein the vicinity information for the first electronic communication device includes information about a second electronic communication device, wherein the information about the second electronic communication device comprises data regarding a proximity or location of the first electronic communication device relative to the second electronic communication device, and wherein the operations further comprise transmitting the information about the second electronic communication device to the one or more of the at least one server and the decentralized infrastructure.

17. The computer-implemented system of claim 16, wherein obtaining information about the second electronic communication device comprises estimating a physical distance between the first electronic communication device and the second electronic communication device based on one or more of an audio signal, a radio-frequency signal, an infrared signal, and an optical signal emitted by one or more of the first electronic communication device and by the second electronic communication device, and by signals between the first and second electronic communication devices and other electronic communication device(s) which are used to estimate the physical distance between the first and second electronic communication devices.

18. The computer-implemented system of claim 15, wherein the status signal is a status of being a physical contact of a person who is positive for a contagion, or more generally, being less than or equal to a specified number of physical contacts separated from a person who is positive for a contagion.

19. The computer-implemented system of claim 15, wherein the user notification is one or more of a text, an animation, and a graphical display, wherein the graphical display comprises information about a dynamically updatable contact proximity network.

20. The computer-implemented system of claim 19, wherein the contact proximity network illustrates a time-evolution of contact network distance(s) from the first user to other users reporting status signals during time windows of interest.

21. The computer-implemented system of claim 15, wherein the vicinity information includes information about a second electronic communication device that comprises one or more of:
 a physical distance of the second electronic communication device from the first electronic communication device; and
 data about audio, radio-frequency, optical, and infrared signals emitted by one or both of the second electronic communication device and the first electronic communication device.

22. The computer-implemented system of claim 15, wherein the contact proximity network traces a spread through the contact proximity network, of the users reporting the specified status signal.

23. The computer-implemented system of claim 22,
 wherein the contact proximity network represents pairwise interactions between the users,
 wherein the contact proximity network comprises proximity information amongst a plurality of the users associated with the plurality of electronic communication devices, wherein the proximity information comprises a geographical distance, a network distance along the contact proximity network, and frequency of contact between users' associated electronic communication devices,
 and wherein the proximity information comprises one or more of:
  current geographical distance between users' associated electronic communication devices, and a current network distance between the users;
  past geographical distance between users' associated electronic communication devices, and a network distance between the users during a past period of time;
  time information related to when users' associated electronic communication devices were within a defined vicinity relative to one another;
  and duration information related to how long users' associated electronic communication devices were within the defined vicinity relative to one another.

24. The computer-implemented system of claim 15, the operations further comprising deriving a predicted spread of the users reporting the specified status signal along at least part of the contact proximity network.

25. The computer-implemented system of claim 15, the operations further comprising outputting a time-evolution graphic depicting a spread of the users reporting the specified status signal along at least part of the contact proximity network, wherein the time-evolution graphic comprises a representation of a number of the users reporting the specified status signal within a specified time window as a function of network distance along the contact proximity network.

26. The computer-implemented system of claim 15, the operations further comprising identifying and outputting a post-exposure notification to the users exposed to a user reporting the specified status signal within a specified time frame.

27. The computer-implemented system of claim 15, the operations further comprising transmitting, to the one or more of the at least one server and the decentralized infrastructure, information about at least one user, wherein the information includes an indicator to report specified status signal(s) on behalf of and associated with the at least one user.

28. The computer-implemented system of claim 15, the operations further comprising outputting an exposure notification indicative of the first user's contact proximity to a second user reporting the specified status signal, wherein the contact proximity to the second user comprises a geographical distance and a network distance along the contact proximity network between the two users.

29. A computer-implemented method, comprising:
 obtaining, by to one or more of at least one server and a decentralized infrastructure and from a first electronic communication device, information about the first electronic communication device, wherein the information about the first electronic communication device comprises vicinity information about a vicinity of the first electronic communication device;
 obtaining a status signal associated with a first user of the first electronic communication device;
 generating and storing, by the one or more of the at least one server and the decentralized infrastructure, a contact proximity network based, in part, on information from the first electronic communication device, and the status signal associated with the first user, wherein the contact proximity network comprises a plurality of interconnected nodes, wherein each node of the plurality of interconnected nodes corresponds to a different user and each pairwise connection between two users in the contact proximity network is based in part upon the two users' current or past relative physical space and time proximity; and
 providing, by the one or more of the at least one server and the decentralized infrastructure and to the first electronic communication device, contact proximity network information about the contact proximity network, wherein the contact proximity network information comprises status signal information associated with the users within the contact proximity network, and
 wherein the contact proximity network information comprises a user notification indicating a network-based proximity of the first user in the contact proximity network to a second user in the contact proximity network, wherein the second user is associated with a specified status signal within a specified time frame, and wherein, for one or more paths of connections between the first user and the second user, the network-based proximity of the first user to the second user corresponds to a path of connection of the one or more paths having a fewest number of connections between the first user and the second user.

30. The computer-implemented method of claim 29, wherein the vicinity information about the vicinity of the first electronic communication device comprises location information of the first electronic communication device.

31. The computer-implemented method of claim 29, wherein the vicinity information about the vicinity of the first electronic communication device comprises data about an environment in which the first electronic communication device is located.

32. The computer-implemented method of claim 29, wherein the vicinity information about the vicinity of the first electronic communication device comprises information about a second electronic communication device.

33. The computer-implemented method of claim 32, wherein the information about the second electronic communication device comprises a physical distance of the first electronic communication device to the second electronic communication device.

34. The computer-implemented method of claim 32, wherein the information about the second electronic communication device comprises information about a wireless local area network, about a wireless access point, or about an electronic communication device in the vicinity of the first electronic communication device.

35. The computer-implemented method of claim 29, wherein obtaining the status signal associated with the first user of the first electronic communication device comprises receiving the status signal from the first electronic communication device or receiving the status signal from a third electronic communication device.

36. The computer-implemented method of claim 29, wherein obtaining the status signal associated with the first user of the first electronic communication device comprises receiving a trusted authentication token, wherein the trusted authentication token authenticates the status signal associated with the first user.

37. The computer-implemented method of claim 29, wherein the user notification is one or more of a text, an animation, and a graphical display.

38. The computer-implemented method of claim 29, wherein the contact proximity network represents pairwise proximal interactions between the users, wherein the contact proximity network comprises proximity information amongst a plurality of users associated with a plurality of electronic communication devices, wherein the proximity information comprises a geographical distance, a network distance along the contact proximity network, and frequency of contact between users' associated electronic communication devices, and wherein the proximity information comprises one or more of:

current geographical distance between users' associated electronic communication devices, and a current network distance between the users;

past geographical distance between users' associated electronic communication devices, and a network distance between the users during a past period of time;

time information related to when users' associated electronic communication devices were within a defined vicinity relative to one another;

and duration information related to how long users' associated electronic communication devices were within the defined vicinity relative to one another.

39. The computer-implemented method of claim 29, wherein the user notification comprises a predicted spread of the users reporting the specified status signal along at least part of the contact proximity network.

40. The computer-implemented method of claim 29, comprising outputting a time-evolution graphic depicting a spread of the users reporting the specified status signal along at least part of the contact proximity network, wherein the time-evolution graphic comprises a representation of a number of the users reporting the specified status signal within a specified time frame as a function of network distance along the contact proximity network.

41. The computer-implemented method of claim 29, comprising identifying and outputting a post-exposure notification to the users exposed to a user reporting the specified status signal within a specified time frame.

42. A computer-implemented system, comprising one or more electronic processors, one or more computer memory devices interoperably coupled with the one or more electronic processors and having tangible, non-transitory, machine-readable media storing one or more instructions that, when executed by the one or more electronic processors, perform one or more operations comprising:

obtaining, by to one or more of at least one server and a decentralized infrastructure and from a first electronic communication device, information about the first electronic communication device, wherein the information about the first electronic communication device comprises vicinity information about a vicinity of the first electronic communication device;

obtaining a status signal associated with a first user of the first electronic communication device;

generating and storing, by the one or more of the at least one server and the decentralized infrastructure, a contact proximity network based, in part, on information from the first electronic communication device, and the status signal associated with the first user, wherein the contact proximity network comprises a plurality of interconnected nodes, wherein each node of the plurality of interconnected nodes corresponds to a different user and each pairwise connection between two users in the contact proximity network is based in part upon the two users' current or past relative physical space and time proximity; and providing, by the one or more of the at least one server and the decentralized infrastructure and to the first electronic communication device, contact proximity network information about the contact proximity network, wherein the contact proximity network information comprises status signal information associated with the users within the contact proximity network, and wherein the contact proximity network information comprises a user notification indicating a network-based proximity of the first user in the contact proximity network to a second user in the contact proximity network, wherein the second user is associated with a specified status signal within a specified time frame, and wherein, for one or more paths of connections between the first user and the second user, the network-based proximity of the first user to the second user corresponds to a path of connection of the one or more paths having a fewest number of connections between the first user and the second user.

43. The computer-implemented system of claim 42, wherein the vicinity information about the vicinity of the first electronic communication device comprises location information of the first electronic communication device.

44. The computer-implemented system of claim 42, wherein the vicinity information about the vicinity of the first electronic communication device comprises data about an environment in which the first electronic communication device is located.

45. The computer-implemented system of claim 42, wherein the vicinity information about the vicinity of the first electronic communication device comprises information about a second electronic communication device.

46. The computer-implemented system of claim 45, wherein the information about the second electronic communication device comprises a physical distance of the first electronic communication device to the second electronic communication device.

47. The computer-implemented system of claim 45, wherein the information about the second electronic communication device comprises information about a wireless local area network, about a wireless access point, or about an electronic communication device in the vicinity of the first electronic communication device.

48. The computer-implemented system of claim 42, wherein obtaining the status signal associated with the first user of the first electronic communication device comprises receiving the status signal from the first electronic communication device or receiving the status signal from a third electronic communication device.

49. The computer-implemented system of claim 42, wherein obtaining the status signal associated with the first user of the first electronic communication device comprises receiving a trusted authentication token, wherein the trusted authentication token authenticates the status signal associated with the first user.

50. The computer-implemented system of claim 42, wherein the user notification is one or more of a text, an animation, and a graphical display.

51. The computer-implemented system of claim 42, wherein the contact proximity network represents pairwise proximal interactions between the users,
wherein the contact proximity network comprises proximity information amongst a plurality of users associated with a plurality of electronic communication devices, wherein the proximity information comprises a geographical distance, a network distance along the contact proximity network, and frequency of contact between users' associated electronic communication devices, and wherein the proximity information comprises one or more of:
current geographical distance between users' associated electronic communication devices, and a current network distance between the users;
past geographical distance between users' associated electronic communication devices, and a network distance between the users during a past period of time;

time information related to when users' associated electronic communication devices were within a defined vicinity relative to one another;
and duration information related to how long users' associated electronic communication devices were within the defined vicinity relative to one another.

52. The computer-implemented system of claim 42, wherein the user notification comprises a predicted spread of the users reporting the specified status signal along at least part of the contact proximity network.

53. The computer-implemented system of claim 42, the operations comprising outputting a time-evolution graphic depicting a spread of the users reporting the specified status signal along at least part of the contact proximity network, wherein the time-evolution graphic comprises a representation of a number of the users reporting the specified status signal within a specified time frame as a function of network distance along the contact proximity network.

54. The computer-implemented system of claim 42, the operations comprising identifying and outputting a post-exposure notification to the users exposed to a user reporting the specified status signal within a specified time frame.

55. A computer-implemented method, comprising:
transmitting, to one or more of at least one server and a decentralized infrastructure and from a first electronic communication device, information about the first electronic communication device, wherein the information about the first electronic communication device comprises vicinity information about a vicinity of the first electronic communication device;
receiving and storing contact proximity network information about a contact proximity network from the one or more of the at least one server and the decentralized infrastructure, wherein the contact proximity network is based, in part, on information from a plurality of electronic communication devices and information about an association between users and the plurality of electronic communication devices, wherein the contact proximity network information comprises status signal information associated with the users within the contact proximity network, wherein the contact proximity network further comprises a plurality of interconnected nodes, and wherein each node of the plurality of interconnected nodes corresponds to a different user and each pairwise connection between two users in the contact proximity network is based in part upon the two users' current or past relative physical space and time proximity; and
based on the contact proximity network information received from the at least one server and the decentralized infrastructure, providing a user notification indicating a network-based proximity of a first user in the contact proximity network to a second user in the contact proximity network, wherein the second user is associated with a specified status signal within a specified time frame,
wherein, for one or more paths of connections between the first user and the second user, the network-based proximity of the first user to the second user corresponds to a path of connection of the one or more paths having a fewest number of connections between the first user and the second user.

56. The computer-implemented method of claim 55, wherein the status signal is a specified status of being a physical contact of a person who is positive for a contagion, or more generally, being less than or equal to a specified number of physical contacts separated from a person who is positive for a contagion.

57. The computer-implemented method of claim 55, wherein the user notification is one or more of a text, an animation, and a graphical display.

58. The computer-implemented method of claim 55, further comprising outputting a time-evolution graphic depicting a spread of the users reporting the specified status signal along at least part of the contact proximity network, wherein the time-evolution graphic comprises a representation of a number of the users reporting the specified status signal within a specified time window as a function of network distance along the contact proximity network.

59. A computer-implemented system, comprising
one or more electronic processors,
one or more computer memory devices interoperably coupled with the one or more electronic processors and having tangible, non-transitory, machine-readable media storing one or more instructions that, when executed by the one or more electronic processors, perform one or more operations comprising:
transmitting, to one or more of at least one server and a decentralized infrastructure and from a first electronic communication device, information about the first electronic communication device, wherein the information about the first electronic communication device comprises vicinity information about a vicinity of the first electronic communication device;
receiving and storing contact proximity network information about a contact proximity network from the one or more of one or more of the at least one server and the decentralized infrastructure, wherein the contact proximity network is based, in part, on information from a plurality of electronic communication devices and information about an association between users and the plurality of electronic communication devices, wherein the contact proximity network information comprises status signal information associated with the users within the contact proximity network, wherein the contact proximity network further comprises a plurality of interconnected nodes, and wherein each node of the plurality of interconnected nodes corresponds to a different user and each pairwise connection between two users in the contact proximity network is based in part upon the two users' current or past relative physical space and time proximity; and
based on the contact proximity network information received from the one or more of the at least one server and the decentralized infrastructure, providing a user notification indicating a network-based proximity of a first user in the contact proximity network to a second user in the contact proximity network, wherein the second user is associated with a specified status signal within a specified time frame,
wherein, for one or more paths of connections between the first user and the second user, the network-based proximity of the first user to the second user corresponds to a path of connection between the first user and the second user having a fewest number of connections.

60. The computer-implemented system of claim 59, wherein the specified status signal is a status of being a physical contact of a person who is positive for a contagion, or more generally, being less than or equal to a specified number of physical contacts separated from a person who is positive for a contagion.

61. The computer-implemented system of claim 59, wherein the user notification is one or more of a text, an animation, and a graphical display, wherein the graphical display comprises information about a dynamically updatable contact proximity network.

62. The computer-implemented system of claim 59, further comprising outputting a time-evolution graphic depicting a spread of the users reporting the specified status signal along at least part of the contact proximity network, wherein the time-evolution graphic comprises a representation of a number of the users reporting the specified status signal within a specified time window as a function of network distance along the contact proximity network.

63. A computer-implemented method, comprising:
obtaining, by one or more of at least one server and a decentralized infrastructure and from a first electronic communication device, information about the first electronic communication device, wherein the information about the first electronic communication device comprises vicinity information about a vicinity of the first electronic communication device;
generating and storing, by the one or more of the at least one server and the decentralized infrastructure, a contact proximity network based, in part, on information from the first electronic communication device, wherein the contact proximity network further comprises a plurality of interconnected nodes, and wherein each node of the plurality of interconnected nodes corresponds to a different user and each pairwise connection between two users in the contact proximity network is based in part upon the two users' current or past relative physical space and time proximity; and
providing, by the one or more of the at least one server and the decentralized infrastructure and to the first electronic communication device, contact proximity network information about the contact proximity network, wherein the contact proximity network information comprises status signal information associated with the users within the contact proximity network, and
wherein the contact proximity network information comprises a user notification indicating a network-based proximity of a first user in the contact proximity network to a second user in the contact proximity network, wherein the second user is associated with a specified status signal within a specified time frame, and
wherein, for one or more paths of connections between the first user and the second user, the network-based proximity of the first user to the second user corresponds to a path of connection between the first user and the second user having a fewest number of connections.

64. The computer-implemented method of claim 63, wherein the user notification is one or more of a text, an animation, and a graphical display, and wherein the graphical display comprises a dynamically updatable chart.

65. The computer-implemented method of claim 63, comprising outputting a time-evolution graphic depicting a spread of the users reporting the specified status signal along at least part of the contact proximity network, wherein the time-evolution graphic comprises a representation of a number of the users reporting the specified status signal within a specified time frame as a function of network distance along the contact proximity network.

66. A computer-implemented system, comprising
one or more electronic processors,
one or more computer memory devices interoperably coupled with the one or more electronic processors and having tangible, non-transitory, machine-readable media storing one or more instructions that, when executed by the one or more electronic processors, perform one or more operations comprising:
obtaining, by one or more of at least one server and a decentralized infrastructure and from a first electronic communication device, information about the first electronic communication device, wherein the information about the first electronic communication device comprises vicinity information about a vicinity of the first electronic communication device;
generating and storing, by the one or more of the at least one server and the decentralized infrastructure, a contact proximity network based, in part, on information from the first electronic communication device, wherein the contact proximity network further comprises a plurality of interconnected nodes, and wherein each node of the plurality of interconnected nodes corresponds to a different user and each pairwise connection between two users in the contact proximity network is based in part upon the two users' current or past relative physical space and time proximity; and
providing, by the one or more of the at least one server and the decentralized infrastructure and to the first electronic communication device, contact proximity network information about the contact proximity network, wherein the contact proximity network information comprises status signal information associated with the users within the contact proximity network, and
wherein the contact proximity network information comprises a user notification indicating a network-based proximity of a first user in the contact proximity network to a second user in the contact proximity network, wherein the second user is associated with a specified status signal within a specified time frame, and
wherein, for one or more paths of connections between the first user and the second user, the network-based proximity of the first user to the second user corresponds to a path of connection between the first user and the second user having a fewest number of connections.

67. The computer-implemented system of claim 66, wherein the user notification is one or more of a text, an animation, and a graphical display, and wherein the graphical display comprises a dynamically updatable chart.

68. The computer-implemented system of claim 66, comprising outputting a time-evolution graphic depicting a spread of the users reporting the specified status signal along at least part of the contact proximity network, wherein the time-evolution graphic comprises a representation of a number of the users reporting the specified status signal within a specified time frame as a function of network distance along the contact proximity network.

* * * * *

UNITED STATES PATENT AND TRADEMARK OFFICE
CERTIFICATE OF CORRECTION

PATENT NO. : 11,950,163 B2
APPLICATION NO. : 17/339779
DATED : April 2, 2024
INVENTOR(S) : Po-Shen Loh et al.

It is certified that error appears in the above-identified patent and that said Letters Patent is hereby corrected as shown below:

In the Claims

Column 60, Line 66, in Claim 56:
Delete "the status signal is a specified" and insert -- the specified status signal is a --.

Column 61, Line 34, in Claim 59:
After "from the" delete "one or more of".

Signed and Sealed this
Fourth Day of June, 2024

Katherine Kelly Vidal
Director of the United States Patent and Trademark Office